(12) United States Patent
Labbe et al.

(10) Patent No.: US 11,708,557 B2
(45) Date of Patent: Jul. 25, 2023

(54) COMPLEX OF MUTUALISTIC MICROBES DESIGNED TO INCREASE PLANT PRODUCTIVITY

(71) Applicant: UT-Battelle, LLC, Oak Ridge, TN (US)

(72) Inventors: Jessy L. Labbe, Oak Ridge, TN (US); Wellington Muchero, Oak Ridge, TN (US); Cyd Elizabeth Hamilton, Oak Ridge, TN (US); Dale A. Pelletier, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 502 days.

(21) Appl. No.: 16/854,154

(22) Filed: Apr. 21, 2020

(65) Prior Publication Data
US 2020/0245629 A1 Aug. 6, 2020

Related U.S. Application Data

(62) Division of application No. 15/334,793, filed on Oct. 26, 2016, now Pat. No. 10,660,340.

(60) Provisional application No. 62/246,394, filed on Oct. 26, 2015, provisional application No. 62/294,048, filed on Feb. 11, 2016.

(51) Int. Cl.
| | |
|---|---|
| *C12N 1/20* | (2006.01) |
| *A01N 63/30* | (2020.01) |
| *A01N 63/27* | (2020.01) |
| *C05F 11/08* | (2006.01) |
| *C12N 1/14* | (2006.01) |
| *C12R 1/39* | (2006.01) |

(52) U.S. Cl.
CPC .............. *C12N 1/205* (2021.05); *A01N 63/27* (2020.01); *A01N 63/30* (2020.01); *C05F 11/08* (2013.01); *C12N 1/14* (2013.01); *C12N 1/20* (2013.01); *C12R 2001/39* (2021.05)

(58) Field of Classification Search
CPC . C12N 1/205; C12N 1/14; C12N 1/20; A01N 63/27; A01N 63/30; C05F 11/08; C12R 2001/39
See application file for complete search history.

(56) References Cited

U.S. PATENT DOCUMENTS

| | | | | |
|---|---|---|---|---|
| 4,045,204 A | ‡ | 8/1977 | Matsunaga | B01J 2/28 71/11 |
| 2012/0015806 A1 | ‡ | 1/2012 | Paikray | A01N 63/30 504/11 |

FOREIGN PATENT DOCUMENTS

| | | |
|---|---|---|
| IE | 922074 A1 | 12/1992 |
| WO | WO 2015/001575 A1 | 1/2015 |
| WO | WO 2015/001575 A1 ‡ | 1/2015 ............. A01N 63/00 |

OTHER PUBLICATIONS

Varma, A. et al., Piriformospora indica, a Cultivable Plant-Growth-Promoting Root Endophyte, Jun. 1999, Applied and Environmental Microbiology, vol. 65, No. 6, pp. 2741-2744. (Year: 1999).*
J. L. Labbé et al., "Newly identified helper bacteria stimulate ectomycorrhizal formation in Populus," Frontiers in Plant Science, Plant-Microbe Interaction, published Oct. 24, 2014, vol. 5, Article 579, p. 1-10.*
Labbe, J.L. et al., "Newly identified helper bacteria stimulate extomyocorrhizal formation in Populus", www.frontiersin.org, (Oct. 2014), vol. 5, Article 579, pp. 1-10.‡
International Search Report dated Feb. 27, 2017 issued in PCT/US16/58816.‡
Meena, K. K. et a., "Co-inoculation of the endophytic fungus Piriformospora indica with the phosphate-solubilising bacterium Pseudomonas striata affects population dynamics and plant growth in chickpea", Biol Fertil Soils, (2009), 6 pages.‡
Zuccaro, A. et al., "Endophytic Life Strategies Decoded by Genome and Transcriptome Analyses of the Mutualistic Root Symbiont Piriformospora indica", PLoS Pathogens, (Oct. 2011), vol. 7, Issue 10, 26 pages.‡
Inviation to Pay Additional Fees dated Dec. 22, 2016 issed in PCT/US16/58816.‡
Deveau, A. et al., "The mycorrhiza helper Pseudomonas fluorescens BBc6R8 has a specific priming effect on the growtth, morphology and gene expression of the ectomycorrhizal fungus Laccaria bicolor S238N", New Phytologist, (2007), vol. 175, pp. 743-755.‡
Frey-Klett, P., "Dose effect in the dual inoculation of an ectomycorrhizal fungus and a mycorrhiza helper bacterium in two forest nurseries", Soil Biology and Biochemistry (1999), vol. 31, pp. 1555-1562.
Larsen, P., "Experimental Systems to Model Nutrient and Carbon Exchange in Plant-Microbe Symbiosis", Genomic Science Contractor-Grantee Meeting XII (2014), pp. 1-2.
Frey, P., "Metabolic and Genotypic Fingerprinting of Fluorescent Pseudomonads Associated with the Douglas Fir-Laccaria bicolor Mycorrhizosphere", Applied and Environmental Microbiology (May 1997), vol. 63, No. 5, pp. 1852-1860.
Swale, B., "Establishment of Douglas Fir Plantations on Bare Ground", [online]. Caverock, 1998 [retrieved on Jun. 18, 2018]. Retrieved from the Intemet:<URL:http://homepages.caverock.net.nz/-bj/d-fir.htm>, 8 pages.
U.S. Office Action dated Sep. 5, 2017 issued in U.S. Appl. No. 15/334,793.
U.S. Office Action dated Mar. 21, 2018 issued in U.S. Appl. No. 15/334,793.
U.S. Office Action dated Jun. 25, 2018 issued in U.S. Appl. No. 15/334,793.

(Continued)

*Primary Examiner* — Monica A Shin
(74) *Attorney, Agent, or Firm* — Scully, Scott, Murphy & Presser, P.C.

(57) ABSTRACT

The present disclosure provides agricultural compositions and methods of using these compositions to increase plant growth, pathogen resistance and drought tolerance. The agricultural compositions disclosed herein comprise mixtures of mutualistic beneficial fungi such as *Laccaria bicolor* and *Piriformispora indica*, and bacterial strains of *Pseudomonas*.

9 Claims, 28 Drawing Sheets

(56) References Cited

OTHER PUBLICATIONS

U.S. Office Action dated Mar. 6, 2019 issued in U.S. Appl. No. 15/334,793.
Notice of Allowance dated Jan. 21, 2020 issued in U.S. Appl. No. 15/334,793.

* cited by examiner
‡ imported from a related application

| Metabolite | Role | Pathogen (Path) | Path1+ Laccaria (Lac) + P indica (Pir) | Path2 +Lac +Pir |
|---|---|---|---|---|
| 6-MBOA | Inhibits microbes | NS | 0.016 | 0.014 |
| HMBOA | Deter herbivores | NS | NS | 0.004 |
| DIMBOA | deter herbivores | NS | 0.019 | NS |

*L. bicolor* S238N

*PMI1_Cenococcum*

*PMI1_Hebeloma*

COMPLEX OF MUTUALISTIC MICROBES DESIGNED TO INCREASE PLANT PRODUCTIVITY

CROSS REFERENCE TO RELATED APPLICATIONS

This application is a divisional of U.S. patent application Ser. No. 15/334,793 filed Oct. 26, 2016, which claims the benefit of priority of U.S. Provisional Application No. 62/246,394, filed Oct. 26, 2015, and U.S. Provisional Application No. 62/294,048, filed Feb. 11, 2016, the entire contents of which are incorporated herein by reference.

STATEMENT REGARDING FEDERALLY SPONSORED RESEARCH OR DEVELOPMENT

This invention was made with government support under Prime Contract No. DE-AC05-000R22725 awarded by the U.S. Department of Energy. The government has certain rights in the invention.

BACKGROUND ART

The majority of terrestrial plants live in association with symbiotic microorganisms, such as fungi which facilitate their access to soil nutrients. The ectomycorrhizal (ECM) symbiosis is the most common association in forest under boreal and temperate climates. Plants harbor a diverse array of asymptomatic fungal foliar and root endosymbionts and have been recovered from all examined plant taxa to date. Several native endophytic and mycorrhizal fungi have been isolated and characterized as promoter of plant host growth and productivity. Concomitantly native bacterial isolates having a plant growth promoting effect and enhancing the fungal-plant beneficial interaction have been characterized as well.

*Populus* is a dominant perennial component of temperate forests having the broadest geographic distribution of any North American tree genus, and is a woody perennial model with high value in pulp, paper and biofuel industries. *Populus* is cultivated worldwide for pulp and paper, veneer, packing material, engineered wood products (e.g., oriented strand board), lumber, and has recently emerged as the preeminent fast-growing woody crop for bioenergy research. *Populus* can be grown on economically marginal agricultural land thereby minimizing the competition between food and fuel production. Moreover, *Populus* is known to associate with a wide variety of root symbiotic microbes. *Populus* is also one of the few plants known to be colonized by both endo- and ectomycorrhizal fungi, making it a unique model system for the study of interactions between plants and microorganisms.

Corn (*Zea mays*, also known as maize) is the most widely grown grain crop throughout the Americas, and a food crop model for bioethanol production in the United States.

The symbiotic fungus *Laccaria bicolor* is a member of Hydnangiaceae (Basidiomycota, Agaricomycotina, Agaricomycetes, Agaricomycetidae, Agaricales), a large family of ectomycorrhizal and saprotrophic basidiomycetes. *Piriformospora indica* (Hymenomycetes, Basidiomycota) is a cultivable endophyte that colonizes roots.

The symbiotic fungus *Hebeloma* is a member of Hymenogastraceae (Basidiomycota, Agaricomycotina, Agaricomycetes, Agaricales, Hymenogastraceae), a large family of ectomycorrhizal and saprotrophic basidiomycetes with a wide range of tree-hosts, and can be found in most woodland ecosystems worlwide. The symbiotic fungus *Cenoccocum* is an ascomycetous fungus placed into the Dothideomycetes, where it represents the only known ectomycorrhizal species within this large and ecologically diverse class of Ascomycota. It is one of the most common and globally abundant genera of ectomycorrhizal fungi, forming black ectomycorrhizas with darkly pigmented hyphae. It has a broad host- and habitat range.

Microbial pathogens, like *Atractiella* (Atr) and *Neonectria*, are detrimental to plant growth. Effective and eco-friendly ways are needed to combat pathogenic microorganisms. Currently the chemical compounds to combat pathogens are also damaging to the environment and possibly human health. The current invention offers a solution with a composition made up of benign and natural microorganisms.

Another important aspect of plant growth is the ability to adapt to arid or drought conditions, which is a trait known as drought tolerance/resistance. Arid conditions can lower the yield of many crops, causing great financial losses. Therefore, methods to increase drought tolerance/resistance in plants are needed. The symbiotic microorganism compositions disclosed herein help plants tolerate dry conditions better.

BRIEF DESCRIPTION OF THE DRAWINGS

FIG. 7A shows plant heights, FIG. 7B shows above-ground fresh biomass, and FIG. 7C shows total leaf area of the *Populus* plants under different treatments.

FIG. 14A: Photo of in vitro cultured *L. bicolor* S238N; FIG. 14B: Diameter of *L. bicolor* S238N colonies cultured with (top curve) or without (bottom curve) GM41; FIG. 14C: Fungal dry weight of *L. bicolor* S238N cultured with (top curve) or without GM41 (bottom curve); FIG. 14D: Photo of in vitro cultured *Cenococcum* PMI1; FIG. 14E: Diameter of *Cenococcum* PMI1 colonies cultured with (top curve) or without (bottom curve) GM41; FIG. 14F: Fungal dry weight of *Cenococcum* PMI1 cultured with (top curve) or without (bottom curve) GM41; FIG. 14G: Photo of in vitro cultured *Hebeloma* spp. PMI1; FIG. 14H: Diameter of *Hebeloma* spp. PMI1 colonies cultured with (top curve) or without (bottom curve) GM41; FIG. 14I: Fungal dry weight of *Hebeloma* spp. PMI1 cultured with (top curve) or without (bottom curve) GM41.

*Pseudomonas fluorescens* GM41, *Laccaria bicolor*, *Cenococcum* spp. PMI1 and *Hebeloma* spp. PMI1. The group of bars on the left represent plants grown under well-watered conditions, and the group of bars on the right represent plants grown under drought conditions. Experiments were performed using 4 replicates of inoculated or non-inoculated *Populus* cuttings; *, ** significantly different ANOVA $p<0.05$.

Figure 19:
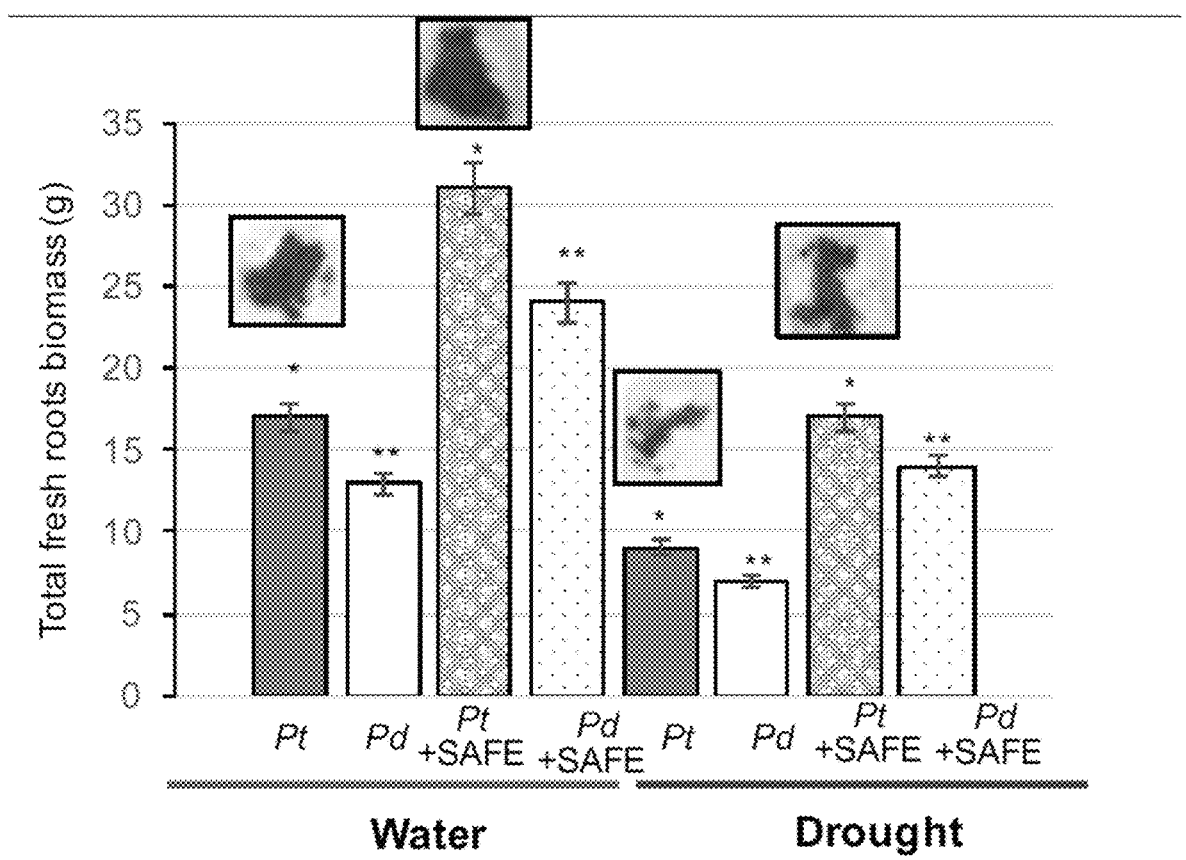

FIG. 19. Effects of SAFE inoculant on the fresh root biomass of *Populus trichocharpa* and *P. deltoides* under well-watered- and drought (−0.5 to −1 MPa) conditions over 3 months in greenhouse. In each group of bars are, from left to right, Pt: *P. trichocarpa*; Pd: *P. deltoides*; Pt+SAFE: mixture of *P. trichocarpa* and *Pseudomonas fluorescens* GM41, *Laccaria bicolor*, *Cenococcum* spp. PMI1 and *Hebeloma* spp. PMI1. Pd+SAFE: mixture of *P. deltoides* and *Pseudomonas fluorescens* GM41, *Laccaria bicolor*, *Cenococcum* spp. PMI1 and *Hebeloma* spp. PMI1. The group of bars on the left represent plants grown under well-watered conditions, and the group of bars on the right represent plants grown under drought conditions. Experiments were performed using 4 replicates of inoculated or non-inoculated *Populus* cuttings; *, ** significantly different ANOVA $p<0.05$.

Figure 20A:
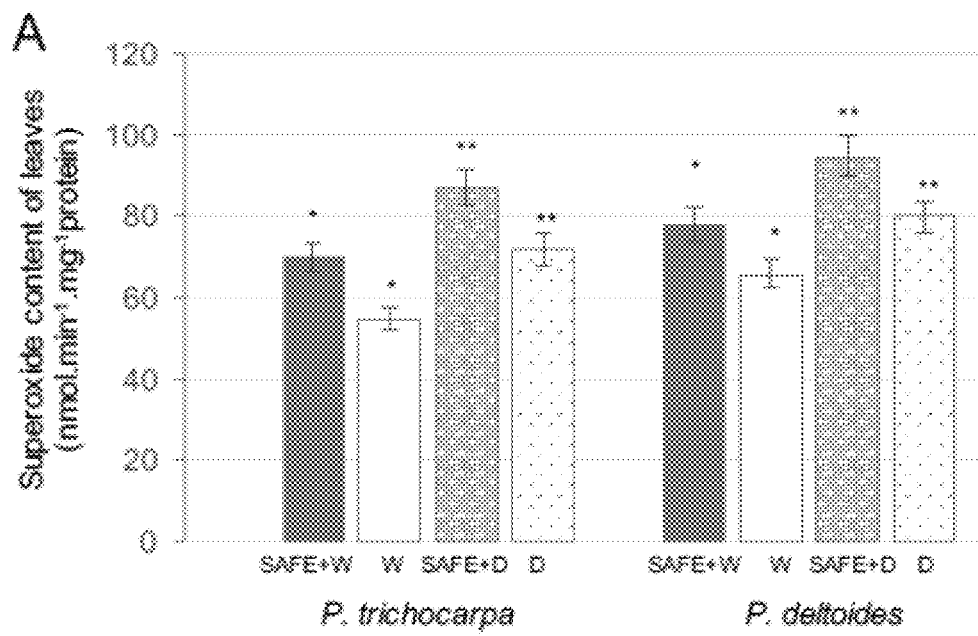
Figure 20B:
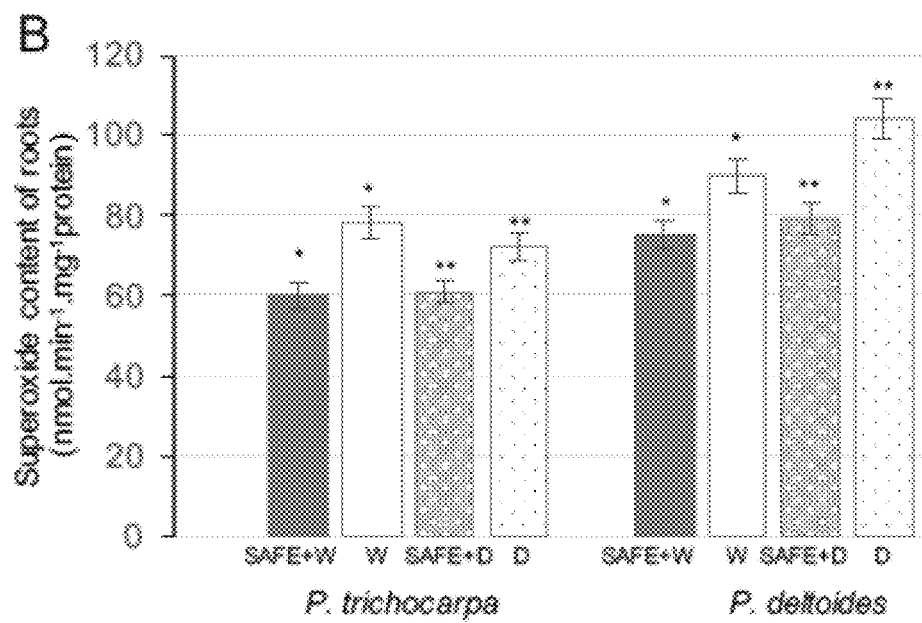

FIG. 20A-20B. Effects of SAFE inoculant on the Superoxide radical content of leaves (FIG. 20A) and roots (FIG. 20B) in *Populus trichocharpa* and *P. deltoides* under well-watered- and drought (−0.5 to −1 MPa) conditions over 3 months in greenhouse. W: well-watered condition; D: drought condition. SAFE: mixture of *Pseudomonas fluorescens* GM41, *Laccaria bicolor*, *Cenococcum* spp. PMI1 and *Hebeloma* spp. PMI1. Experiments were performed using 4 replicates of inoculated or non-inoculated *Populus* cuttings; *, ** significantly different ANOVA $p<0.05$.

Figure 21:
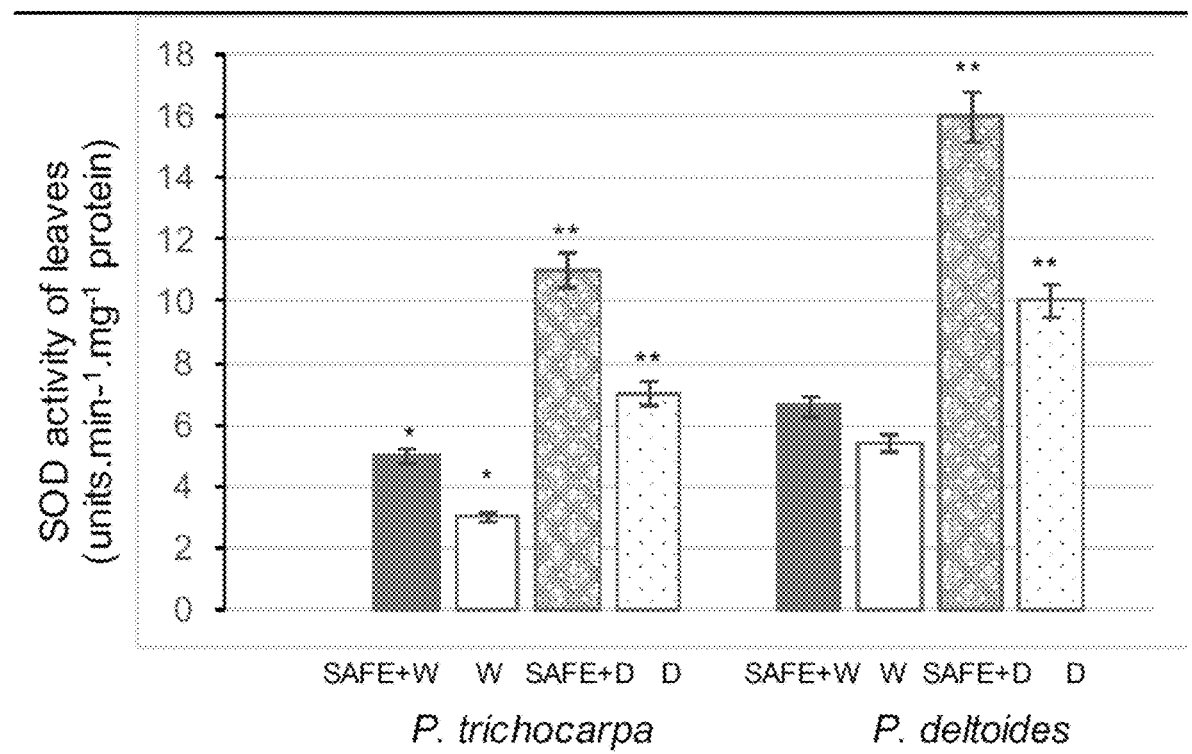

FIG. 21. Effects of SAFE inoculant on the Superoxide Oxide Dismutase (SOD) activity of leaves in *Populus trichocharpa* and *P. deltoides* under well-watered- and drought (−0.5 to −1 MPa) conditions over 3 months in greenhouse. W: well-watered condition; D: drought condition. SAFE: mixture of *Pseudomonas fluorescens* GM41, *Laccaria bicolor*, *Cenococcum* spp. PMI1 and *Hebeloma* spp. PMI1. Experiments were performed using 4 replicates of inoculated or non-inoculated *Populus* cuttings; *, ** significantly different ANOVA $p<0.05$.

Figure 22:
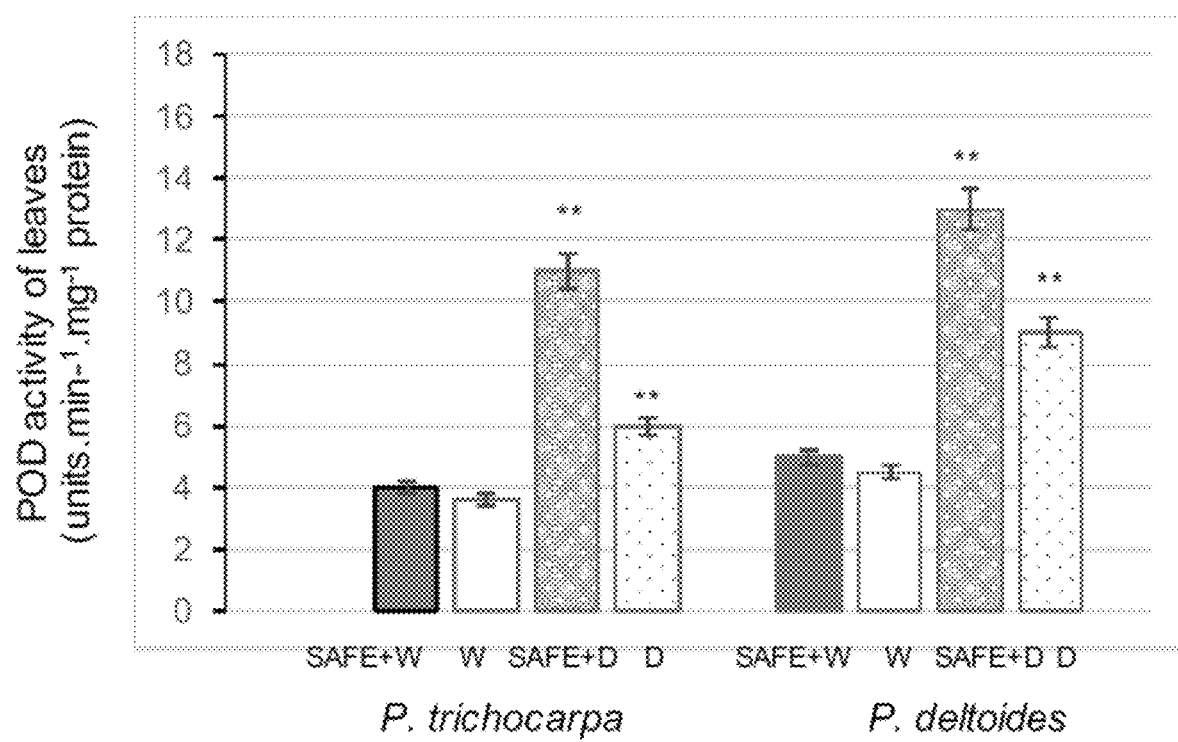

FIG. 22. Effects of SAFE inoculant on the Peroxidase (POD) activity of leaves in *Populus trichocharpa* and *P. deltoides* under well-watered- and drought (−0.5 to −1 MPa) conditions over 3 months in greenhouse. W: well-watered condition; D: drought condition. SAFE: mixture of *Pseudomonas fluorescens* GM41, *Laccaria bicolor*, *Cenococcum* spp. PMI1 and *Hebeloma* spp. PMI1. Experiments were performed using 4 replicates of inoculated or non-inoculated *Populus* cuttings; *, ** significantly different ANOVA $p<0.05$.

Figure 23:
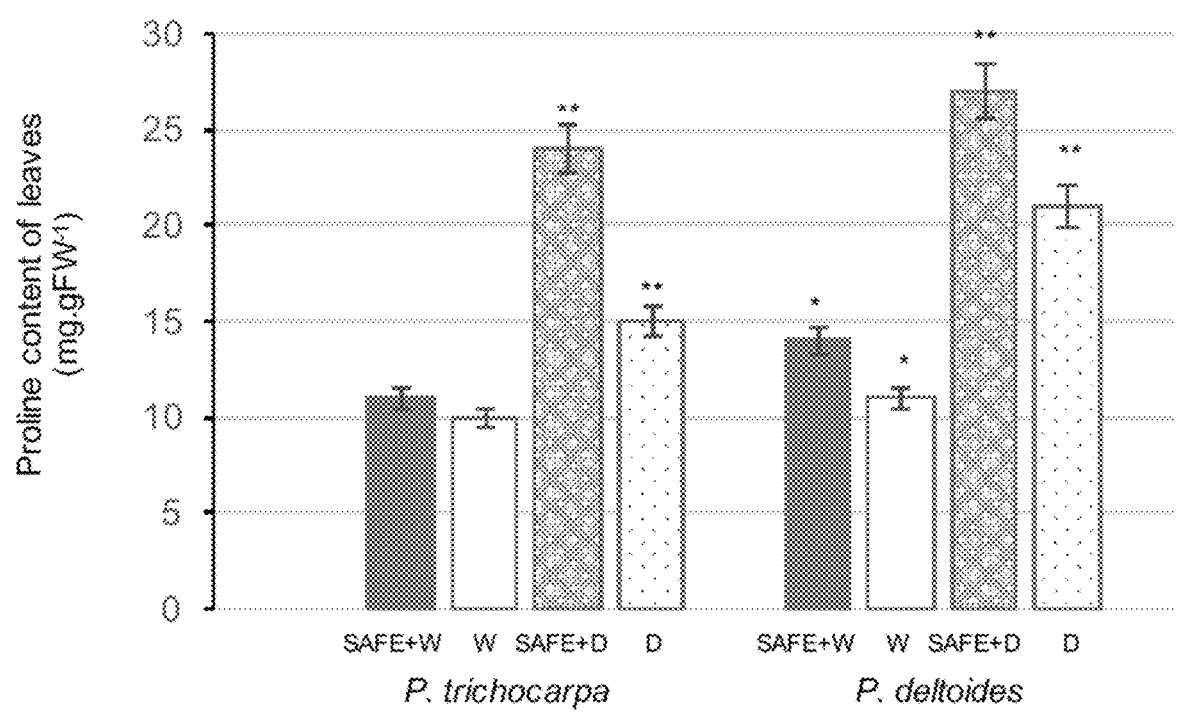

FIG. 23. Effects of SAFE inoculant on the proline content of leaves in *Populus trichocharpa* and *P. deltoides* under well-watered- and drought (−0.5 to −1 MPa) conditions over 3 months in greenhouse. W: well-watered condition; D: drought condition. SAFE: mixture of *Pseudomonas fluorescens* GM41, *Laccaria bicolor*, *Cenococcum* spp. PMI1 and *Hebeloma* spp. PMI1. Experiments were performed using 4 replicates of inoculated or non-inoculated *Populus* cuttings; *, ** significantly different ANOVA $p<0.05$.

Figure 24A:
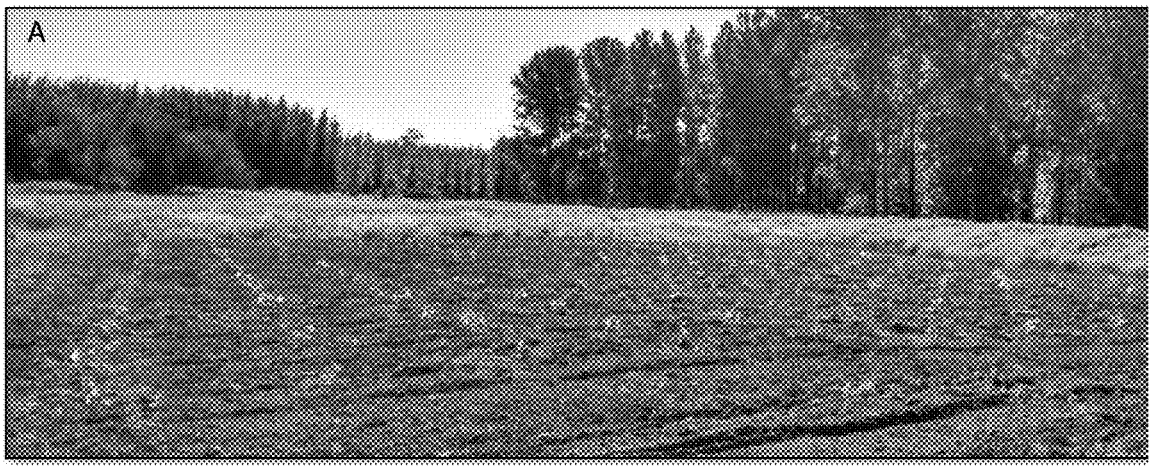
Figure 24B:
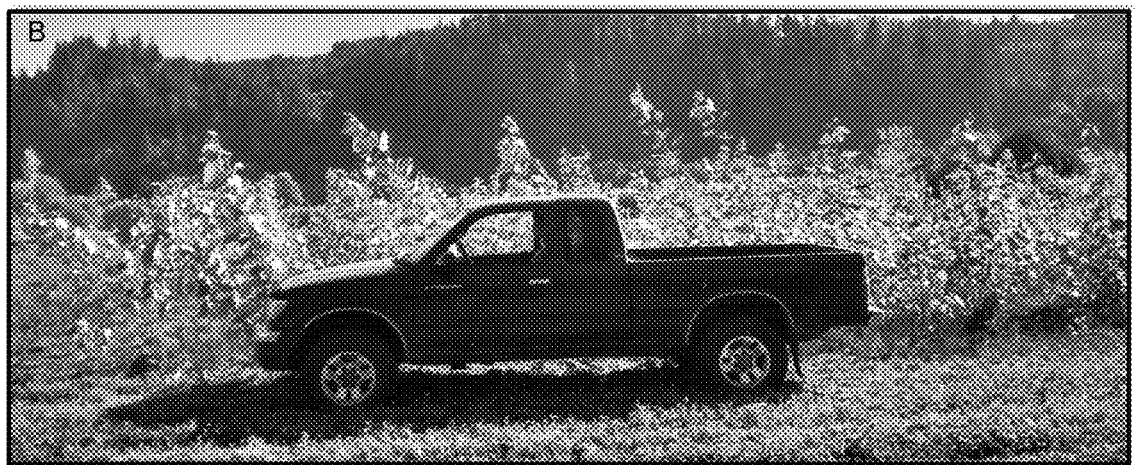

FIG. 24A-24B. Field deployment with or without SAFE inoculation of GreenWood Resources, Inc. commercial genotypes of *Populus* in Westport, Oreg. A: beginning of the growing season in April; B: end of the growing season in October of the same year.

Figure 25A:
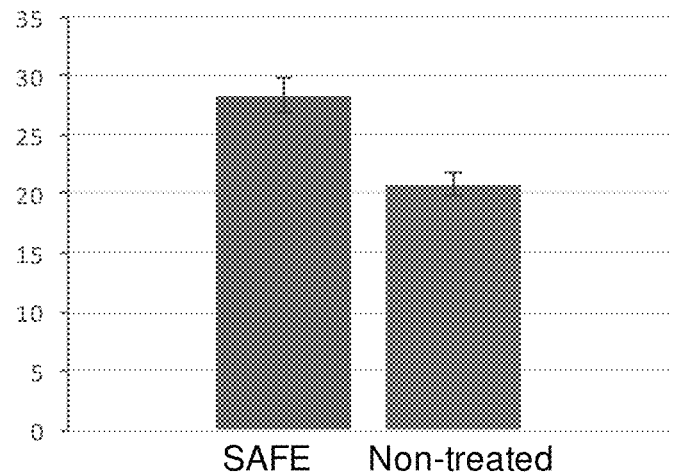
Figure 25B:
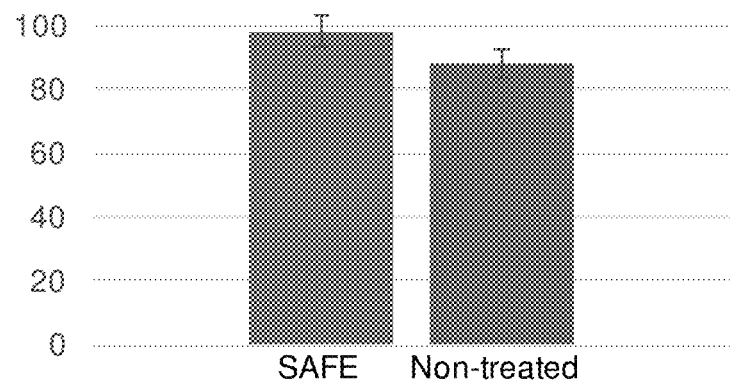

FIG. 25A-25B. Plant size (FIG. 25A) and survival (FIG. 25B) after one month of growth in field with or without SAFE inoculation. A total of 60 inoculated and 60 non-inoculated plants have been used for statistical analyses. FIG. 25A represents plant size after one month of growth in field with (left bar) and without (right bar) SAFE microbial mixture. FIG. 25B represents survival of the plants to natural pathogens after one month of growth in field with (left bar) and without (right bar) SAFE microbial mixture.

Figure 26:
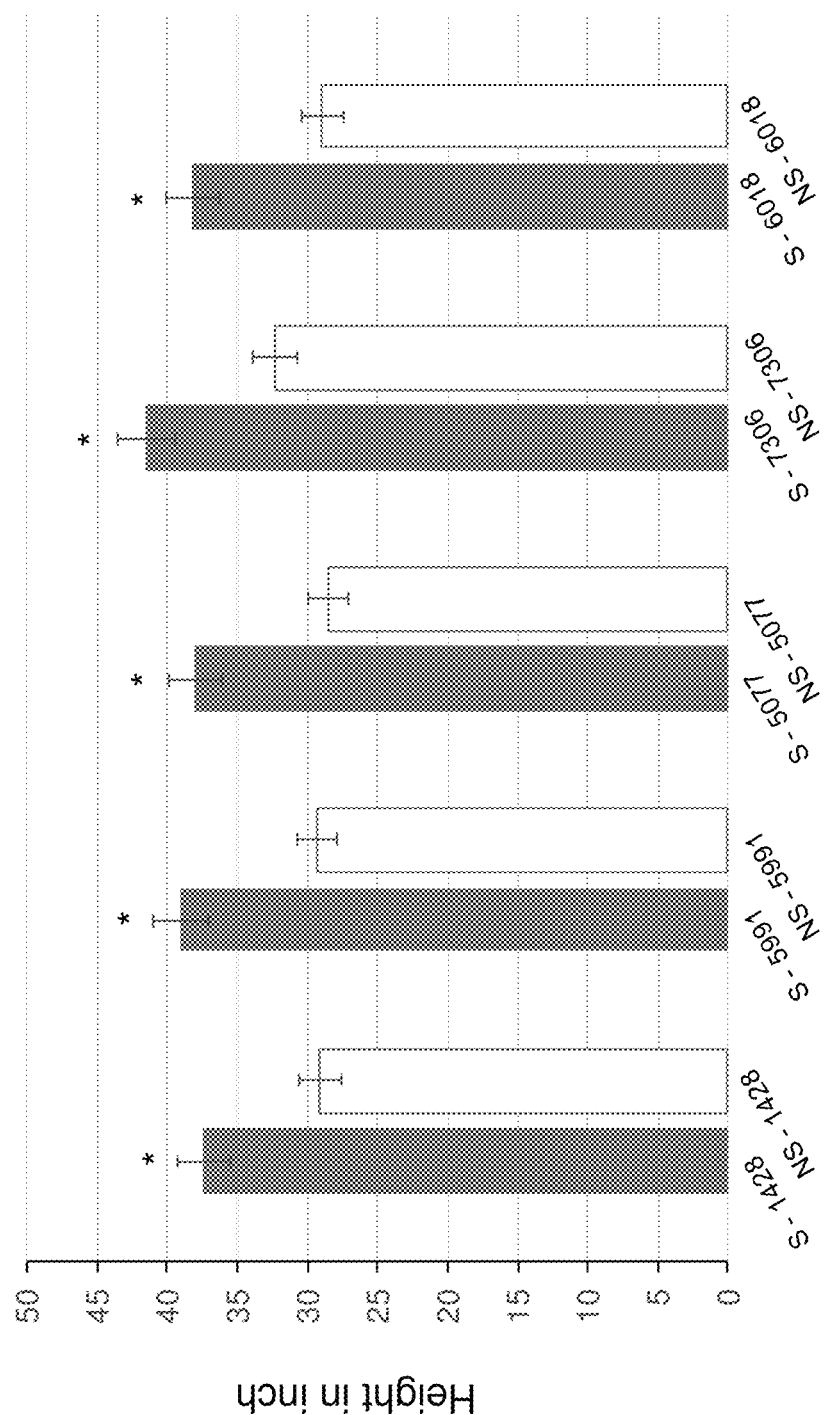

FIG. 26. Plant height (in inch) after four months of growth in field with or without SAFE inoculation. The first bar (solid) in each group represents a *Populus* plant inoculated with SAFE mixture (S) and the second bar (empty) in each group represents a *Populus* plant that is not inoculated with SAFE mixture (NS). A total of 60 inoculated and 60 non-inoculated plants have been used for statistical analyses. Experiments were performed using 12 replicates of inoculated or non-inoculated *Populus* cuttings of 5 commercial genotypes from GreenWood Resources, Inc.; *, ** significantly different ANOVA $p<0.05$.

Figure 27:
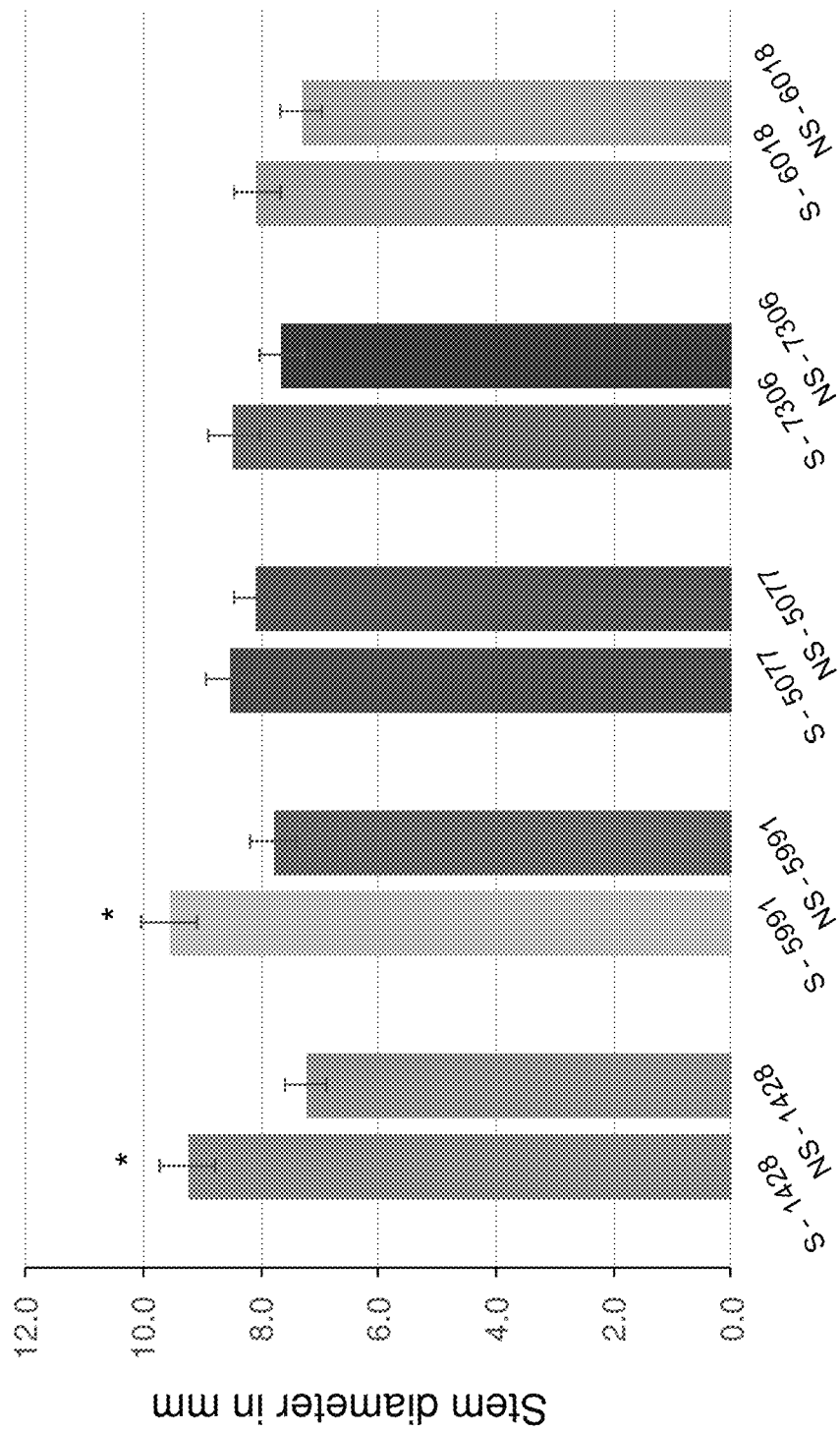

FIG. 27. Stem diameter (in mm) of *Populus* plants after four months of growth in field with or without SAFE inoculation. The first bar in each group represents a *Populus* plant inoculated with SAFE mixture (S), and the second bar in each group represents a *Populus* plant that is not inoculated with SAFE mixture (NS). A total of 60 inoculated and 60 non-inoculated plants were used for statistical analyses. Experiments were performed using 12 replicates of inoculated or non-inoculated *Populus* cuttings of 5 commercial genotypes from GreenWood Resources, Inc.; *, ** significantly different ANOVA $p<0.05$.

Figure 28:
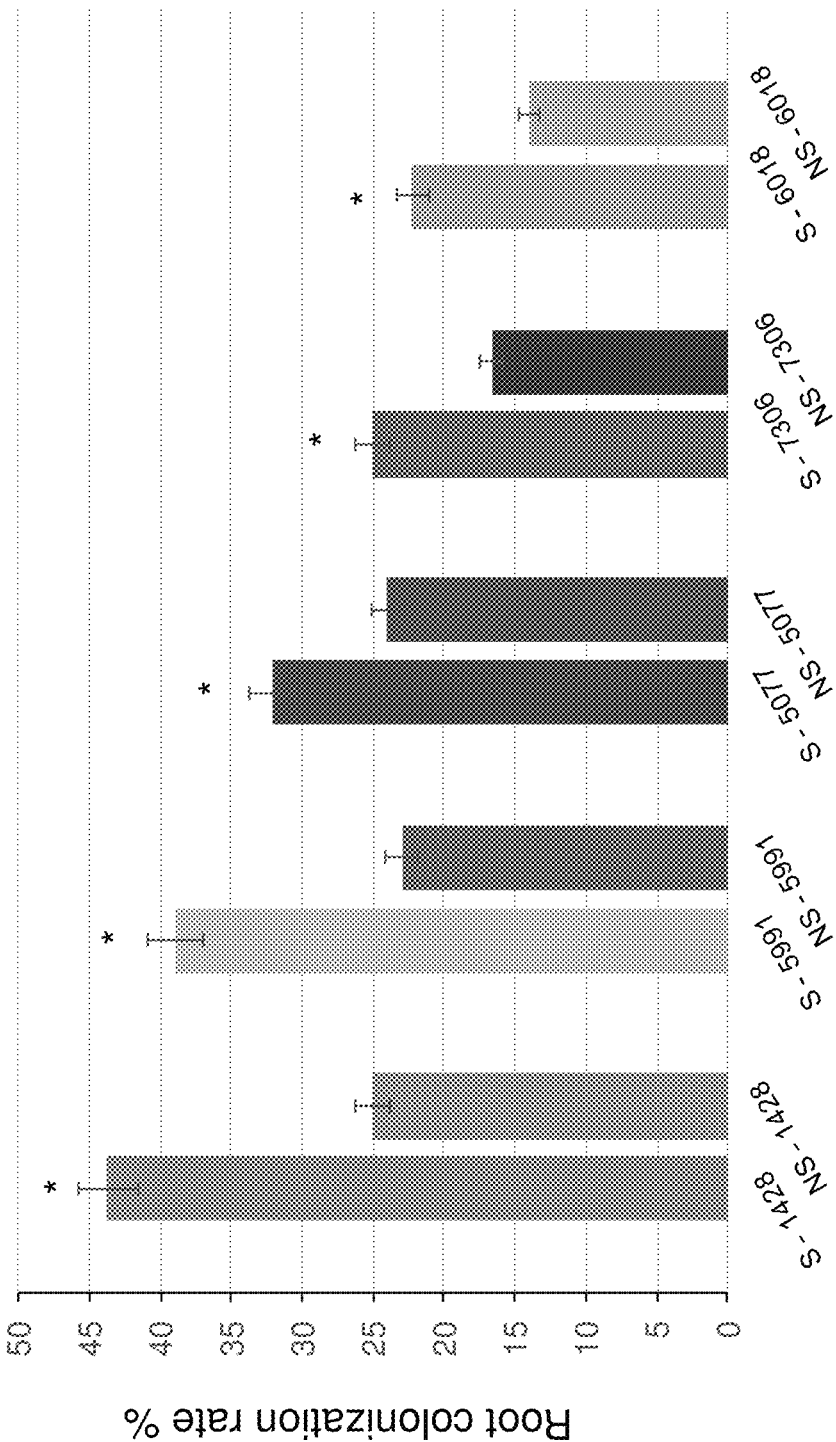

FIG. 28. Root colonization rate by in situ soil microbes (and SAFE microbes when inoculated). The first bar in each group represents a *Populus* plant inoculated with SAFE mixture (S) and the second bar in each group represents a *Populus* plant that is not inoculated with SAFE mixture (NS). A total of 60 inoculated and 60 non-inoculated plants were used for statistical analyses. Experiments were performed using 12 replicates of inoculated or non-inoculated *Populus* cuttings of 5 commercial genotypes from GreenWood Resources, Inc.; *, ** significantly different ANOVA $p<0.05$.

DETAILED DESCRIPTION OF THE INVENTION

Both fungal and bacterial isolates have a wide geographic and plant host species distribution. So far only a few studies have examined the role of constructed microbial communities for plants. However, these studies lacked data on constructed microbial communities on woody hosts. These studies have also failed to identify mechanisms that are critical to produce stable, scalable, mutualistic outcomes. Most research to-date on utilization of mutualistic symbiotum to increase crop fitness has a poor field-trial record. One possible explanation for the failure in the field is that most past research has focused on a single species of a mutualistic organism in the field and it is possible that a single microorganism may not be able to compete with the resident microorganisms in the heterogeneous environment of the soil. Research into utilization of complex, constructed microbial communities to increase not only plant host yields but also the efficacy of this approach in a diversity of hosts and geographic contexts, is almost non-existent.

The present inventors have investigated the impact of a constructed multiple-microbial member community (hereinafter "proprietary microbial blend" or "PMB" or "PMB mixture" or "SAFE mixture") on poplar and corn growth and found significantly higher biomass yields at the greenhouse scale relative to controls not exposed to the constructed microbial community. PMB is a microbial composition including at least two beneficial fungi, or a mixture of one or more beneficial fungi with bacteria that have been categorized as Mycorrhiza Helper Bacteria (MHB), such as strains of *Pseudomonas fluorescens*. The presence of more than one beneficial microorganism helps establish the beneficial endo- or ectomycorrhizal (ECM) symbiosis when the beneficial microorganisms cooperate, and also provides redundancy in many different contexts, for example, where a single beneficial microorganism may be competed out by resident microorganisms in the soil.

PMB can be formulated as liquid or solid formulations (such as granulated or powdered pellets, or prills), as well as in slow or controlled release formulations. In solid formulations, PMBs can include binding agents such as pullulan, paraffin, pitch or calcium nitrate.

Figures 3, 4:
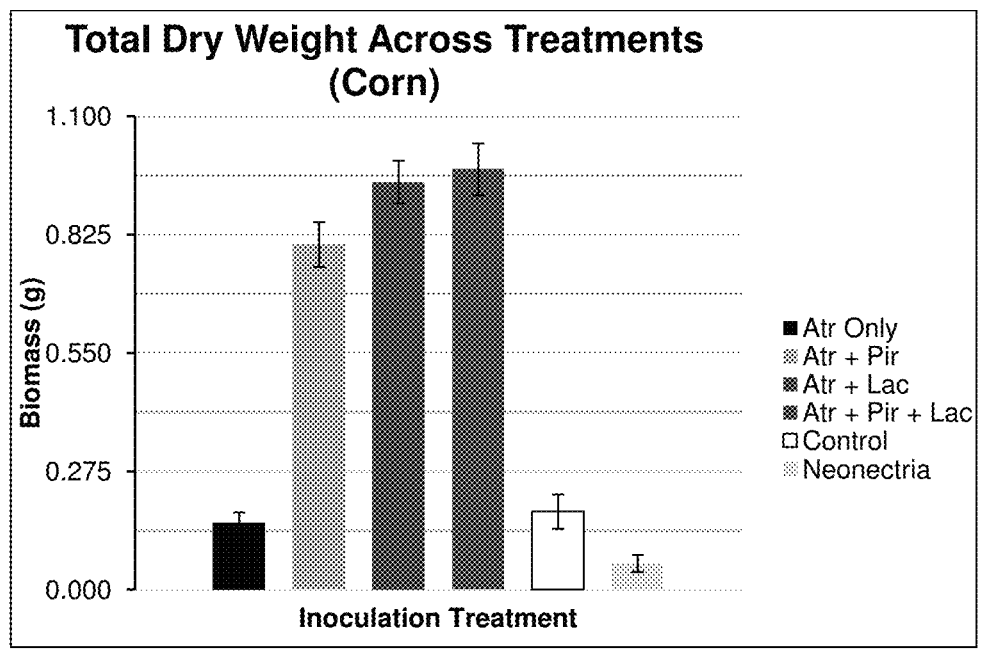
FIG. 3. Biomass production of corn plants treated with pathogenic or beneficial fungi. Bars from left to right represent biomasses of corn plants treated with *Atractiella* (Atr), *Atractiella* and *P. indica* (Pir), *Atractiella* and *L. bicolor* (Lac), *Atractiella* and *P. indica* (Pir) and *L. bicolor* (Lac), Control, and finally *Neonectria*. Control means not fungal inoculation occurred; *Atractiella* (Atr) and *Neonectria* are pathogenic to corn, while *P. indica* (Pir) and *L. bicolor* (Lac) significantly increase total plant biomass (roots and shoots) they also appear to rescue plants from colonization by a pathogenic fungus.
FIG. 4. Metabolites affected by beneficial fungi Lac and Pir. Potential causal mechanisms for results found in FIG. 2 are identified in this table. When both Lac and Pir are present in combination with the pathogen metabolites responsible for increase pest resistance are up-regulated compared to control treatments. Interestingly these inhibitory metabolites are also involved in pathways leading to herbivore resistance and/or deterrence.

There are many pathogenic microorganisms in the soil, and when a plant is infected with a pathogen, the growth of the plant is blunted. Pathogens cause a decline in plant biomass production and crop yield. The present inventors discovered that PMB that contains at least two beneficial fungi, such as *L. bicolor* and *P. indica*, can prevent pathogen-induced growth suppression (FIG. 3). Some embodiments of the PMB further contain at least one additional other beneficial fungal strain, such as *Hebeloma* spp. and *Cenoccocum* spp. Combination of beneficial fungi in PMB provides redundancy to the microbial blend and makes it useful in different soil conditions and with different plant varieties.

The inventors have also discovered that PMB induces beneficial changes in host plant metabolite profile, which, without being bound in any one theory, may explain the increased pest and pathogen resistance by the host plant (FIG. 4).

The inventors have also reported several *Pseudomonas fluorescens* strains, including isolates GM21, GM25, GM30, GM48, GM49, GM50, GM55, GM60, GM67, GM74, GM78, GM79, GM80, GM84, GM102, GM18 and GM41, that display mycorrhizal helper effect when used with beneficial fungi. Among all the strains, GM41 showed the most beneficial effect. *Pseudomonas fluorescens* GM41 strain was deposited at the American Type Culture Collection (ATCC, 10801 University Boulevard, Manassas, Va. 20110 USA) on Jan. 20, 2016. The deposit was made under the terms of the Budapest Treaty. GM41 has been assigned the Accession number PTA-122788.

The inventors have observed that, in combination with a mycorrhizal fungal strain such as *L. bicolor*, GM41 enhances the beneficial effect the fungal strain has on plant, further increasing plant yield and stress tolerance (FIG. 7A-7D).

Therefore, this disclosure provides compositions comprising PMB and methods of using PMB for improving resistance to pests, increasing plant yields (biomass and fruit/grain), and improving resistance/tolerance to abiotic stresses such as salt and drought.

In one aspect, this disclosure provides compositions useful for promoting plant growth and improving plant resistance to pests and to stress conditions.

To prepare the compositions of this disclosure, fungal inocula can be prepared in 1 L of sterile soil or 1 L of millet. After total fungal growth (i.e., growth to saturation), a fungal inoculum of 1 L is obtained. This inoculum is mixed with a plant soil to obtain a final soil used to grow plants. The term "volume to volume" refers to a ratio of the volume of an inoculum to the volume of final soil; e.g., 1 L inoculum soil with 9 L of plant soil makes 10% volume to volume. For field applications, 5 to 20% volume to volume (i.e., volume of inoculum soil vs. volume of final soil) is generally used, which is equivalent to 1 L to 4 L of fungal inoculum/m$^2$ of final soil. The final concentration range of fungi in the final soil is generally 5 to 20 fungal cells/g of final soil.

In another embodiment, fungal inocula can be prepared in 1 L of culture media (e.g., potato dextrose broth). After total fungal growth (i.e., growth to saturation), liquid culture are mixed with sterile water to until a concentration of 50 cells (per fungal species)/ml. This final fungal solution is mixed along with an alginic acic/alginate solution (10 grams/Liter). This mixture can either 1) be poured into a 100 g/L-CaCl$_2$ solution with a burette and dropped as small pellets (~5 mm) to encapsulate the fungal solution in alginate beads; or 2) be poured on granulates or soil beads then transferred to a 100 g/L-CaCl$_2$ solution to coat the fungal solution on the granulates or soil beads. The final concentration range of fungi in the final soil is generally 5 to 20 fungal cells/g of final soil.

In another embodiment, 5 ml of a liquid bacterial culture at a concentration of $1 \times 10^2$-$1.6 \times 10^6$ CFU/ml can be applied per L of final soil or culture media containing fungi as described above. For example, if the total soil volume is 10 L (1 L fungal inoculum+9 L of final soil), 50 ml of a liquid bacterial culture can be added to the soil.

In yet another embodiment, bacteria and fungi can be co-cultured in the same inoculum soil.

In one embodiment, a composition includes a mixture of a *L. bicolor* strain and a *P. indica* strain. In some embodiments, the composition comprises a mixture of a *L. bicolor* strain and a *P. indica* strain at about 100 total fungal cells per gram of the composition, or about 100 fungal cells per strain per gram of the composition. The term "about 100" refers to any number falling within the range of 85-115, i.e., including 85, 90, 95, 100, 105, 110 and 115. In one specific embodiment, the *L. bicolor* is of the strain S238N.

In another embodiment, a composition includes a mixture of a *L. bicolor* strain and a *P. indica* strain, and further includes a strain of *Pseudomonas fluorescens*. In specific embodiments, the composition includes between $1 \times 10^2$ CFU and $1.6 \times 10^6$ CFU bacterial cells per milliliter of the composition. In a particular embodiment, the composition includes a mixture of a *L. bicolor* strain and a *P. indica* strain, and a strain of *Pseudomonas fluorescens* at $5 \times 10^2$ CFU/mL of the composition. In some embodiments, the strain of *Pseudomonas fluorescens* is selected from one of the following isolates: GM21, GM25, GM30, GM48, GM49, GM50, GM55, GM60, GM67, GM74, GM78, GM79, GM80, GM84, GM102, GM18, and pGM41. In a specific embodiment, the strain of *Pseudomonas fluorescens* is GM41.

In still another embodiment, a composition includes a mixture of *L. bicolor* strain and a strain of *Pseudomonas fluorescens*. In specific embodiments, the composition includes a mixture of a *L. bicolor* strain at about 100 fungal cells per gram of the composition and a liquid bacterial inoculum between $1 \times 10^2$ CFU/mL and $1.6 \times 10^6$ CFU/mL. In a specific embodiment, the composition includes $5 \times 10^2$ CFU/mL of a *Pseudomonas fluorescens* strain. In a specific embodiment, the strain of *L. bicolor* is S238N and the strain of *Pseudomonas fluorescens* is selected from one of the following isolates: GM21, GM25, GM30, GM48, GM49, GM50, GM55, GM60, GM67, GM74, GM78, GM79, GM80, GM84, GM102, GM18 and GM41. In a specific embodiment, the strain of *Pseudomonas fluorescens* is GM41.

In another embodiment, a composition includes a mixture of a *L. bicolor* strain, a strain of *Pseudomonas fluorescens* and a strain of *Cenoccocum* spp. In specific embodiments, the composition includes a mixture of a *L. bicolor* strain at about 100 fungal cells per gram of the composition, a *Cenoccocum* spp. strain at about 100 fungal cells per gram of the composition and a liquid bacterial inoculum between $1 \times 10^2$ CFU/mL and $1.6 \times 10^6$ CFU/mL. In a specific embodiment, the composition includes $5 \times 10^2$ CFU/mL of a *Pseudomonas fluorescens* strain. In a specific embodiment, the strain of *L. bicolor* is S238N and the strain of *Pseudomonas fluorescens* is selected from one of the following isolates: GM21, GM25, GM30, GM48, GM49, GM50, GM55, GM60, GM67, GM74, GM78, GM79, GM80, GM84, GM102, GM18 and GM41. In a specific embodiment, the strain of *Pseudomonas fluorescens* is GM41. In a specific embodiment, the strain of *Cenoccocum* spp. is PMI1.

In even yet another embodiment, a composition includes a mixture of a *L. bicolor* strain, a strain of *Pseudomonas fluorescens*, a strain of *Cenoccocum* spp. and a strain of *Hebeloma* spp. In specific embodiments, the composition includes a mixture of a *L. bicolor* strain at about 100 fungal cells per gram of the composition, a *Hebeloma* spp. strain at about 100 fungal cells per gram of the composition, a *Cenoccocum* spp. strain at about 100 fungal cells per gram of the composition and a liquid bacterial inoculum between $1 \times 10^2$ CFU/mL and $1.6 \times 10^6$ CFU/mL. In a specific embodiment, the composition includes $5 \times 10^2$ CFU/mL of a *Pseudomonas fluorescens* strain. In a specific embodiment, the strain of *L. bicolor* is S238N and the strain of *Pseudomonas fluorescens* is selected from one of the following isolates: GM21, GM25, GM30, GM48, GM49, GM50, GM55, GM60, GM67, GM74, GM78, GM79, GM80, GM84, GM102, GM18 and GM41. In a specific embodiment, the strain of *Pseudomonas fluorescens* is GM41. In a specific embdiment, the strain of *Hebeloma* spp. is PMI1. In a specific embodiment, the strain of *Cenoccocum* spp. is PMI1.

In another embodiment, a composition includes a mixture of a *L. bicolor* strain, a strain of *Pseudomonas fluorescens* and a strain of *Hebeloma* spp. In specific embodiments, the composition includes a mixture of a *L. bicolor* strain at about 100 fungal cells per gram of the composition, a *Hebeloma* spp. strain at about 100 fungal cells per gram of the composition and a liquid bacterial inoculum between $1 \times 10^2$ CFU/mL and $1.6 \times 10^6$ CFU/mL. In a specific embodiment, the composition includes $5 \times 10^2$ CFU/mL of a *Pseudomonas fluorescens* strain. In a specific embodiment, the strain of *L. bicolor* is S238N and the strain of *Pseudomonas fluorescens* is selected from one of the following isolates: GM21, GM25, GM30, GM48, GM49, GM50, GM55, GM60, GM67, GM74, GM78, GM79, GM80, GM84, GM102, GM18 and GM41. In a specific embodiment, the strain of *Pseudomonas fluorescens* is GM41. In a specific embodiment, the strain of *Hebeloma* spp. is PMI1.

In yet another embodiment, a composition includes a mixture of a *P. indica* strain and a strain of *Pseudomonas fluorescens*. In some embodiments, the composition includes a mixture of a *P. indica* strain at about 100 fungal cells per gram of the composition and a liquid inoculum of a strain of *Pseudomonas fluorescens* at between $1 \times 10^2$ CFU/mL and $1.6 \times 10^6$ CFU/mL. In a specific embodiment, the composition contains $5 \times 10^2$ CFU/mL of a strain of *Pseudomonas fluorescens*. In specific embodiments, the strain of *Pseudomonas fluorescens* is selected from one of the following isolates GM21, GM25, GM30, GM48, GM49, GM50, GM55, GM60, GM67, GM74, GM78, GM79, GM80, GM84, GM102, GM18, and GM41. In a specific embodiment, the strain of *Pseudomonas fluorescens* is GM41.

The compositions disclosed herein can include, in addition to the desirable microorganisms, other components suitable for plant growth, including phosphorus and certain trace elements such as copper, iron, manganese, zinc, cobalt, molybdenum, and boron, as oxides or salts containing the elements in the cationic form.

The compositions disclosed herein, if necessary, may also contain additional components suitable for agriculture or fertilizer use, such as a water-soluble material. Suitable water-soluble materials are starch, dextrin, gum arabic, gelatin, casein, glue, methylcellulose, carboxymethylcellulose, hydroxyalkylcellulose, alginic acid, polyvinylalcohol, polyacrylic acid, polyacrylamid, and a modified form thereof substituted partially by hydrophobic radicals in place of hydrophilic radicals. Among these water-soluble materials, starch, dextrin, gum arabic, gelatin, casein, glue, methylcellulose, carboxymethylcellulose and hydroxyalkylcellulose are preferred. The additional incorporation of said water-soluble material is optional and the amount to be added is not limited, but is usually up to 50 parts by weight for 100 parts by weight of final composition.

The compositions disclosed herein, if necessary, may also contain a binding agent selected from the group consisting of pullulan, paraffin, pitch and calcium nitrate. The present molded composition may be manufactured by any shaping method; the customary granulation technique, customary compression molding technique or customary extrusion molding technique may be conveniently used.

The compositions disclosed herein can be in solid form, and can also be in liquid form; and can include, in addition to the desirable microorganisms, other components suitable for plant growth, including phosphorus and certain trace elements such as copper, iron, manganese, zinc, cobalt, molybdenum, and boron, as oxides or salts containing the elements in the cationic form in an agriculturally acceptable liquid carrier such as water.

According to the present methods, the soil in a field can be treated with a composition disclosed herein at 1 L/m$^2$ to 10 L/m$^2$. One specific embodiment treats the soil in the field with 5 L/m$^2$ of a composition mixture (i.e. 5 liters of PMB per 1 m$^2$ of soil). In some embodiments, a composition containing a fungal inoculum of about 100 fungal cells/gram is applied to a final soil at a 5 to 20% volume to volume ratio (i.e., volume of inoculum soil vs. volume of final soil) to achieve about 5 to 20 fungal cells/gram of the final soil. In other embodiments, a composition additionally contains a bacterial strain at a concentration $1 \times 10^2$ CFU/mL-$1.6 \times 10^6$ CFU/mL is applied to a final soil at a 5 to 20% volume to volume dilution.

In another aspect, the disclosure provides methods of treating plants with a microbial composition disclosed herein. The compositions disclosed herein can be applied to a wide array of crops (bioenergy, forage, and food), worldwide and are believed to increase nutrient availability in soils and soil quality, resulting in increased nutrient and moisture uptake by plant roots, leading to increased plant growth.

Example 1: Root Colonization Rates of Different *L. bicolor* Strains on Different Poplar Genotypes Materials and Methods: Root Colonization Measurements:

The percentage of mycorrhizal colonization, as described by Tagu et al. (*Variation in the ability to form ectomycorrhizas in the F1 progeny of an interspecific poplar (Populus spp.) cross*. Mycorrhiza 10:237-240, 2001) was determined three-and-a-half months after inoculation by eight observers. All the observers observed randomly the plants within eight blocks and block after block. Each root system was rinsed with tap water, cut in 1-cm pieces and analyzed under a dissecting microscope. For each root system, 100 apices were randomly examined and assessed as mycorrhizal or non-mycorrhizal.

Different poplar genotypes (particularly poplar genotype 52 225 (*P. deltoides*), poplar genotype D124 (hybrid TXD), poplar genotype ILL 101 (hybrid TXD) and poplar genotype 93 968 (*P. trichocarpa*) were treated with various *L. bicolor* strains (particularly Lb 445.79, Lb 559.96, Lb 594.96, Lb 560.89, Lb 669.97, Lb 561.97, and Lb S238N) and root colonization percent was measured.

Figure 1:
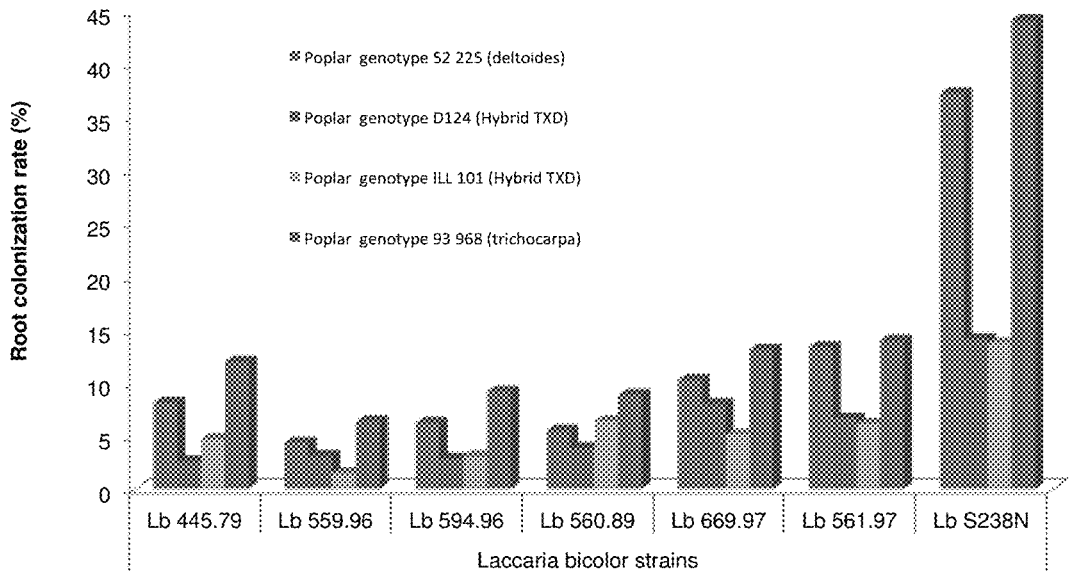
FIG. 1. Root colonization rates of different *L. bicolor* strains on different Poplar genotypes. Different Poplar genotypes (particularly poplar genotype 52 225 (*P. deltoides*), poplar genotype D124 (hybrid TXD), poplar genotype ILL 101 (hybrid TXD) and poplar genotype 93 968 (*P. trichocarpa*) were treated with various *L. bicolor* strains (particularly Lb 445.79, Lb 559.96, Lb 594.96, Lb 560.89, Lb 669.97, Lb 561.97, and Lb S238N) and root colonization percent was measured. In each group of bars in the Figure, from left to right, are poplar genotype 52 225 (*P. deltoides*), poplar genotype D124 (hybrid TXD), poplar genotype ILL 101 (hybrid TXD) and poplar genotype 93 968 (*P. trichocarpa*). Each group of poplar genotypes were treated with *L. bicolor* strains, from left to right, Lb 445.79, Lb 559.96, Lb 594.96, Lb 560.89, Lb 669.97, Lb 561.97, and Lb S238N. Lb S238N gave superior root colonization across all poplar genotypes tested.

Results:

Among all the *L. bicolor* strains, Lb S238N gave better root colonization than all other strains across all poplar genotypes tested (FIG. 1).

Example 2: *Pseudomononas* Strain GM41 Assists *L. bicolor* in Promoting *P. trichocarpa* Growth Materials and Methods:

Various *L. bicolor* strains (particularly Lb 445.79, Lb 559.96, Lb 594.96, Lb 560.89, Lb 669.97, Lb 561.97, and Lb S238N) were applied to *P. trichocarpa* plants between 5-10% volume ratio alone or in combination with 5 ml/L of *Pseudomonas fluorescens* GM41 $10^2$ CFU/ml. The soil was treated using 5 L/m$^2$ of the mixture (i.e. 5 liters of PMB per 1 m$^2$ of soil).

Figure 2:
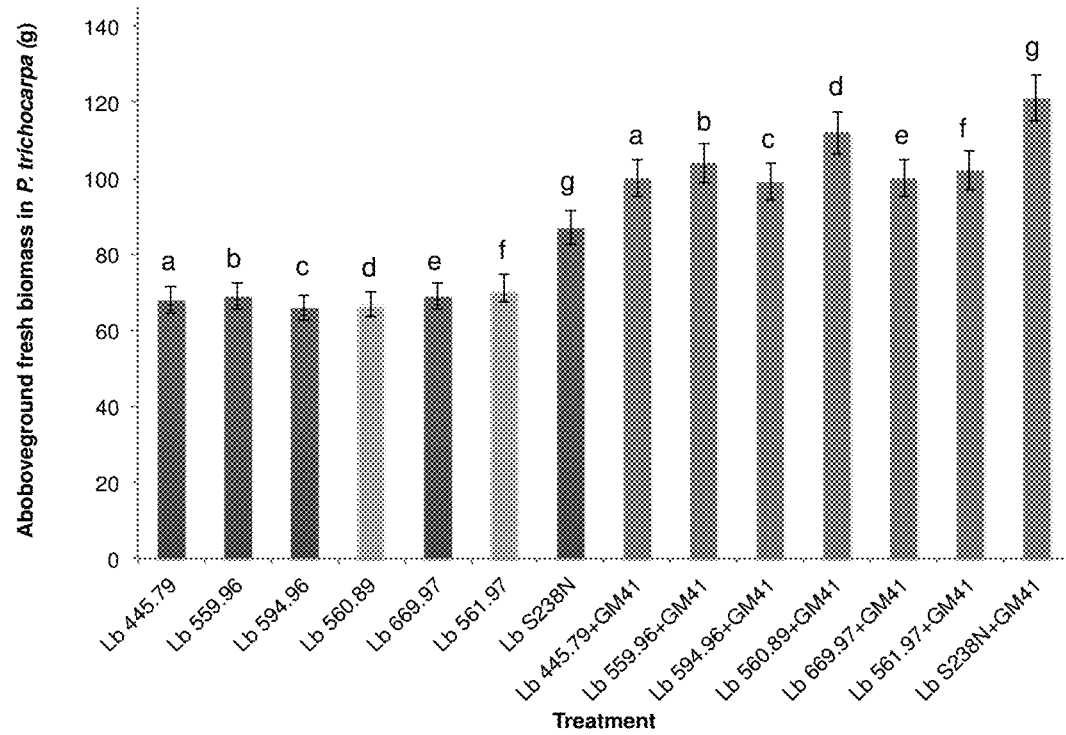
FIG. 2. *Pseudomonas* strain GM41 enhances plant growth when given with different *L. bicolor* strains. *Populus trichocarpa* was incubated either with different *L. bicolor* strains alone (particularly Lb 445.79, Lb 559.96, Lb 594.96, Lb 560.89, Lb 669.97, Lb 561.97, or Lb S238N) (left, labeled a-g) or in combination with *Pseudomonas fluorescens* strain GM41 (right, labeled a-g). Addition of GM41 significantly enhances the above-ground fresh biomass of *P. trichocarpa*.

Results:

GM41 increased the growth of *P. trichocarpa* plants in combination with all *L. bicolor* strains tested (FIG. 2). Lb S238N strain promoted *P. trichocarpa* growth the most, both alone and in combination with GM41 (FIG. 2).

Example 3: Proprietary Microbial Blend (PMB) Comprising *L. bicolor* and *P. indica* Promotes Plant Growth Even in the Presence of Pathogens Materials and Methods:

The dikaryotic mycelium of *L. bicolor* S238N used in this study was grown and maintained in Petri dishes containing Pachlewski agar medium P5 (Di Battista et al., 1996) and incubated at 25° C. for 3 week.

Experiments have been performed using fungal inocula grown in soil/medium mixture or millet before co-culture with plants. At the time of the co-culture with the plants, sterile potting soil has been mixed Volume to Volume with the fungal inoculum. For example, 5% Volume of inoculum to Volume of soil mixture means that 50 ml of the fungal soil has been mixed with 950 ml of sterile soil to grow the plant.

Figure 5:
FIG. 5. Corn growth in growth chamber, responding to inoculation with pathogenic or mutualistic fungi. Pathogenic fungal inoculations on left hand side of picture; mutualistic inoculation treatments on right hand side of picture.
Figure 6:
FIG. 6. Poplar growth in response to commensalistic, mutualistic, and pathogenic (antagonistic) fungi under greenhouse conditions. Plants treated with commensalistic, mutualistic or pathogenic fungi are grown in the green house. Plants are randomly arranged.

Results:

Application of PMB, comprising a mixture of *Piriformispora indica* in combination with *Laccaria bicolor* at 5% volume to volume ratio, equivalent to 1 L/m$^2$ of inoculum at a concentration of 5 cells/g final soil, resulted in increased plant growth by corn regardless of present of pathogenic fungus. When pathogen was present in the absence of the mixture, plant growth was severely stunted (see FIG. 3 and FIG. 5).

Example 4: Proprietary Microbial Blend (PMB) Treatment Increases Beneficial Metabolite Levels in Plants Materials and Methods: Metabolite Profiling—

Individual metabolites were analyzed by metabolite profiling using gas chromatography-mass spectrometry (GC-MS). Briefly, 50-75 mg of finely ground fresh tissue sample were repeatedly extracted with 2.5 ml of 80% ethanol, with the extracts then combined. A 1 ml aliquot was dried in a nitrogen stream. After dissolving the dried extracts in acetonitrile followed by trimethylsilylation, metabolite profiling was performed by GC-MS, as described elsewhere (Jung H W et al., "*Priming in systemic plant immunity*", Science 2009, 324(5923):89-91. Metabolites were identified based on mass spectral fragmentation patterns of electron impact ionization (70 eV) and were quantified using peak areas of a characteristic mass-to-charge (m/z) ratio normalized to the internal standard (sorbitol) recovered and corrected for sample weight. Some of the unidentified metabolites were denoted by their retention time (RT) and key m/z ratio. The metabolite data were presented as fold changes of the transgenic line (average of 3 independent lines with 3 replicates for each line) vs. the average of the controls. Statistical significance was assessed using Student's t-test.

Results:

Metabolites involved in inhibiting microbes (6-MBOA), and deterring herbivores (HMBOA and DIMBOA) were found to be significantly increased in plants treated with the PMB containing *L. bicolor* and *P. indica* strains (FIG. 4). This result at least partially explains the growth advantage of plants treated with the PMB.

Example 5: Proprietary Microbial Blend (PMB) Comprising *L. bicolor* and *Pseudomonas* Increases Drought Resistance in *Populus* Plants Materials and Methods: Testing Drought Tolerance—

Experiments have been performed using 4 replicates of inoculated non-inoculated *Populus* cuttings. Initially, the well-watered *Populus* plants were stressed to −0.5 MPa, at which time they were re-watered to soil capacity. After the plants have been acclimated with three dry down cycles to −0.5 MPa, the plants were further dried down to a greater stress level of −1.0 MPa.

Figure 7A:
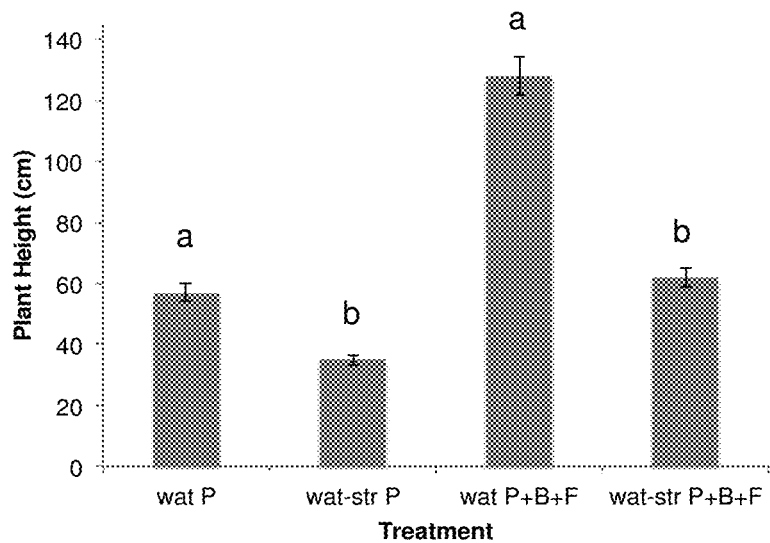
FIGS. 7A-7C. Effects of microbial inoculants in *Populus* grown over 3 months under well watered- and water-stressed (−1 MPa) conditions. P: *Populus* control plant; B: helper bacteria (*Pseudomonas*), F: fungus *Laccaria*. Experiments have been performed using 4 replicates of inoculated non-inoculated *Populus* cuttings (ANOVA p<0.05); a are significantly different, b are significantly different.
Figure 7B:
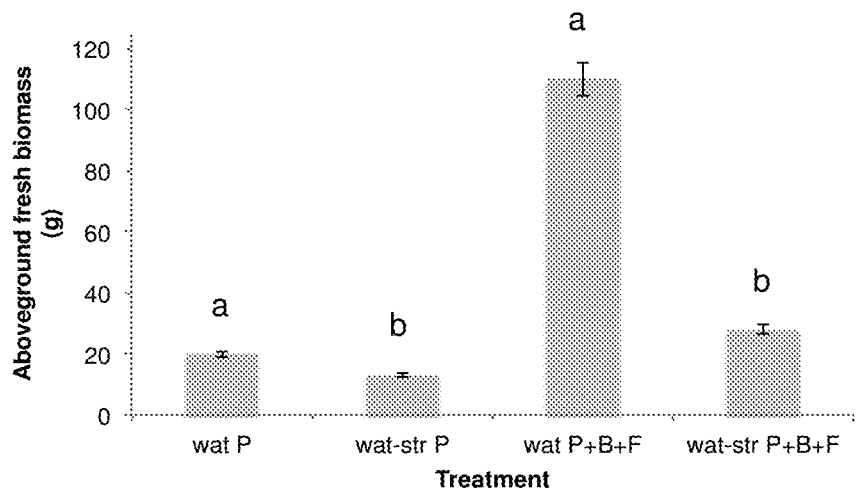
Figure 7C:
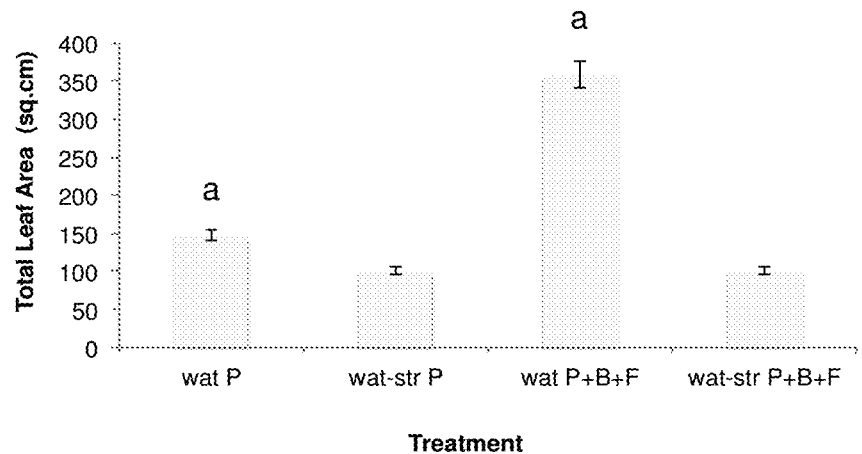

Results:

Application of *L. bicolor* between 5-10% volume ratio in combination with 5 ml/L of *Pseudomonas fluorescens* GM41 at $10^2$ CFU/ml resulted in increased plant growth in poplar in regular condition and as well under light drought stress. Application of *L. bicolor*—GM41 microbial mixture enhances water stress tolerance and a fast recovery from the stress with return of optimal watering conditions (FIGS. 7A-7C).

Example 6: Proprietary Microbial Blend (PMB) Comprising *L. bicolor, P. indica* and *Pseudomonas* Increases the Germination Frequency of Corn Kernel in Greenhouse, but to a Lesser Extent than *P. indica* Alone Materials and Methods:

Corn plants were treated with the microbial mixture comprising 50 cells/ml of *Laccaria bicolor,* 50 cells/ml of *Piriformispora indica* and 1.4 million of CFU/ml *Pseudomonas fluorescens* strain GM41. Germination frequencies of corn kernels were measured in corn plants with or without PMB inoculation.

Figure 8:
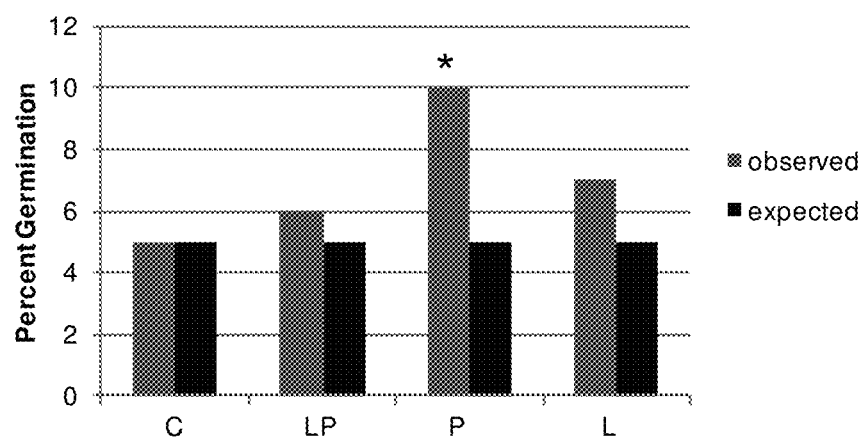
FIG. 8. Germination frequency of corn kernel in greenhouse. In each group of bars in the figure are observed percent germination frequency (left) and expected germination frequency (right) of corn kernels. C: control (no inoculation); LP: inoculation with *Laccaria bicolor* and *Piriformispora indica*; P: inoculation with *Piriformispora indica*; L: inoculation with *Laccaria bicolor*. * Significantly different ANOVA P<0.05.

Results:

Application of *L. bicolor, P. indica* and *P. fluorescens* resulted in an increase in germination frequency of corn kernels in a greenhouse setting (FIG. 8). However, application of *P. indica* alone resulted in a greater increase in germination frequency of corn kernels than the microbial mixture (FIG. 8).

Example 7: Proprietary Microbial Blend (PMB) Comprising *L. bicolor, P. indica* and *Pseudomonas* Did not Result in an Increase in Aboveground Biomass in Corn Plants Materials and Methods:

Corn plants were treated with the microbial mixture comprising 50 cells/ml of *Laccaria bicolor,* 50 cells/ml of *Piriformispora indica* and 1.4 million of CFU/ml *Pseudomonas fluorescens* strain GM41.

Figure 9:
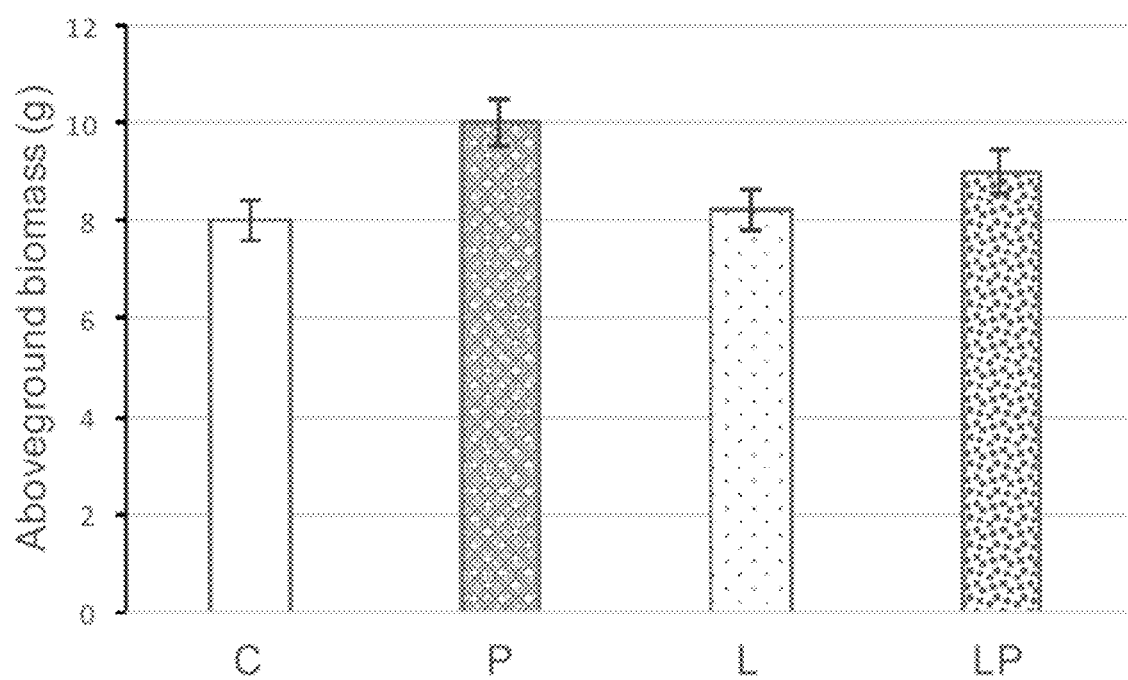
FIG. 9. Aboveground biomass of corn grown after 6-weeks growth in greenhouse. The bars in the Figure, from left to right, are C: control no inoculation; P: inoculation with *Piriformispora indica*; L: inoculation with *Laccaria bicolor*; LP: inoculation with *Laccaria bicolor* and *Piriformispora indica*.

Results:

PMB microbial mix (*L. bicolor* and *P. indica*) did not significantly increase the aboveground biomass of corn while inoculation compared to control (FIG. 9). Interestingly, *P. indica* alone resulted in a greater increase in aboveground biomass than either *L. bicolor* or *P. indica* applied alone (FIG. 9).

Example 8: Proprietary Microbial Blend (PMB) Comprising *L. bicolor, P. indica* and *Pseudomonas* Increases the Germination Frequency of Corn Kernel in Field Materials and Methods:

Corn plants were treated with the microbial mixture comprising 50 cells/ml of *Laccaria bicolor,* 50 cells/ml of *Piriformispora indica* and 1.4 million of CFU/ml *Pseudomonas fluorescens* strain GM41.

Figure 10:
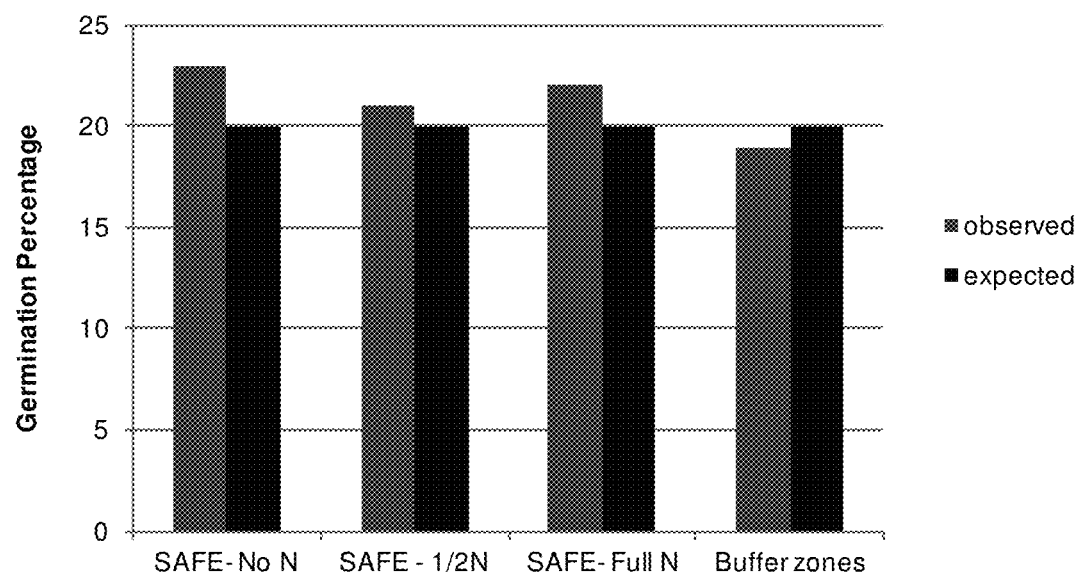
FIG. 10. Germination frequency of corn kernel in field. In each group of bars in the figure are observed percent germination frequency (left) and expected germination frequency (right) of corn kernels. SAFE-No N: inoculation with *Laccaria bicolor, Piriformispora indica* and no nitrogen fertilization; SAFE-1/2N: inoculation with *Laccaria bicolor, Piriformispora indica* and nitrogen fertilization during half of the growing season; SAFE-Full N: inoculation with *Laccaria bicolor, Piriformispora indica* and nitrogen fertilization during the full growing season; Buffer zones: no inoculation and no nitrogen fertilization.

Results:

Application of *L. bicolor, P. indica* and *P. fluorescens* (PMB, or SAFE microbial mixture) resulted in an increase in germination frequency of corn kernels in field no Nitrogen (no N), low Nitrogen (low N) or high Nitrogen (high N) fertilization conditions (FIG. 10).

Figure 12:
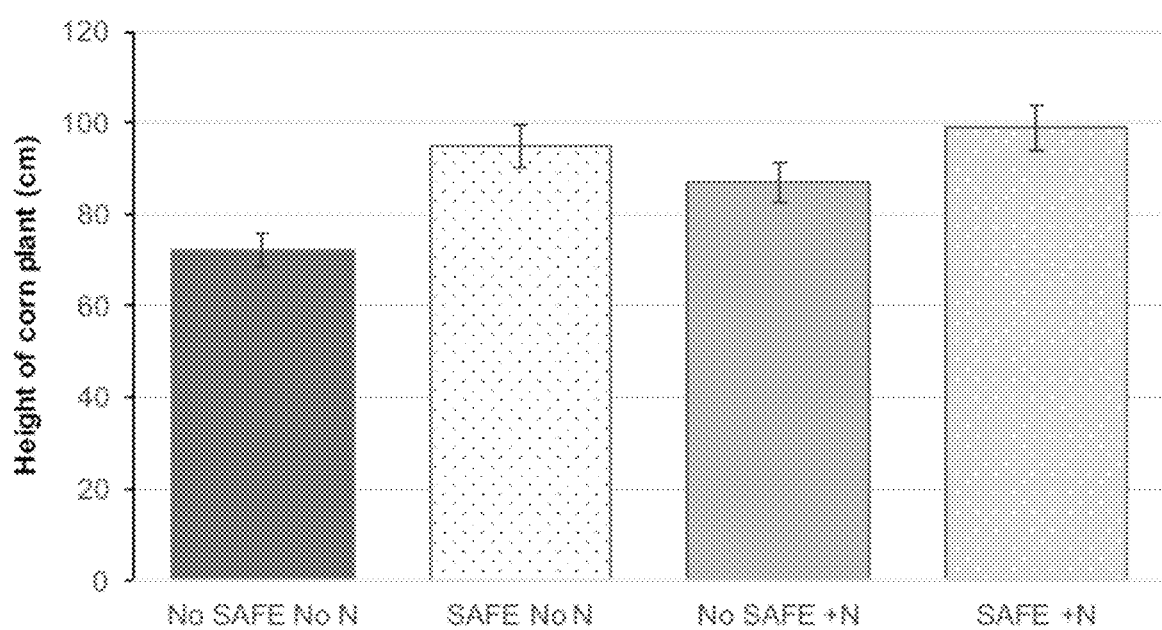
FIG. 12. Average height of corn plant (cm) at the end of the growing season in field. No SAFE No N: no inoculation with SAFE microbial mix (*L. bicolor* and *P. indica*) and no nitrogen-fertilization (the first bar in the figure); SAFE No N: inoculation with SAFE microbial mix (*L. bicolor* and *P. indica*) and no nitrogen-fertilization (the second bar in the figure); No SAFE+N: no inoculation with SAFE microbial mix (*L. bicolor* and *P. indica*) and nitrogen-fertilization (the third bar in the figure); SAFE+N: inoculation with SAFE microbial mix (*L. bicolor* and *P. indica*) and nitrogen-fertilization (the fourth bar in the figure).

Application of *L. bicolor, P. indica* and *P. fluorescens* (PMB, or SAFE microbial mixture) with or without nitrogen fertilization resulted in an increase in corn plant height as compared to non-inoculated controls over the period of the growth season (FIG. 12).

Example 9: Proprietary Microbial Blend (PMB) Comprising *L. bicolor, P. indica* and *Pseudomonas* Increases the Nutritive Qualities of the Soil Materials and Methods:

Phosphorus, ammonia nitrogen and nitrate nitrogen levels were measured in a soil sample treated with PMB, but no nitrogen fertilization throughout the growing season (June through September).

Figure 11:
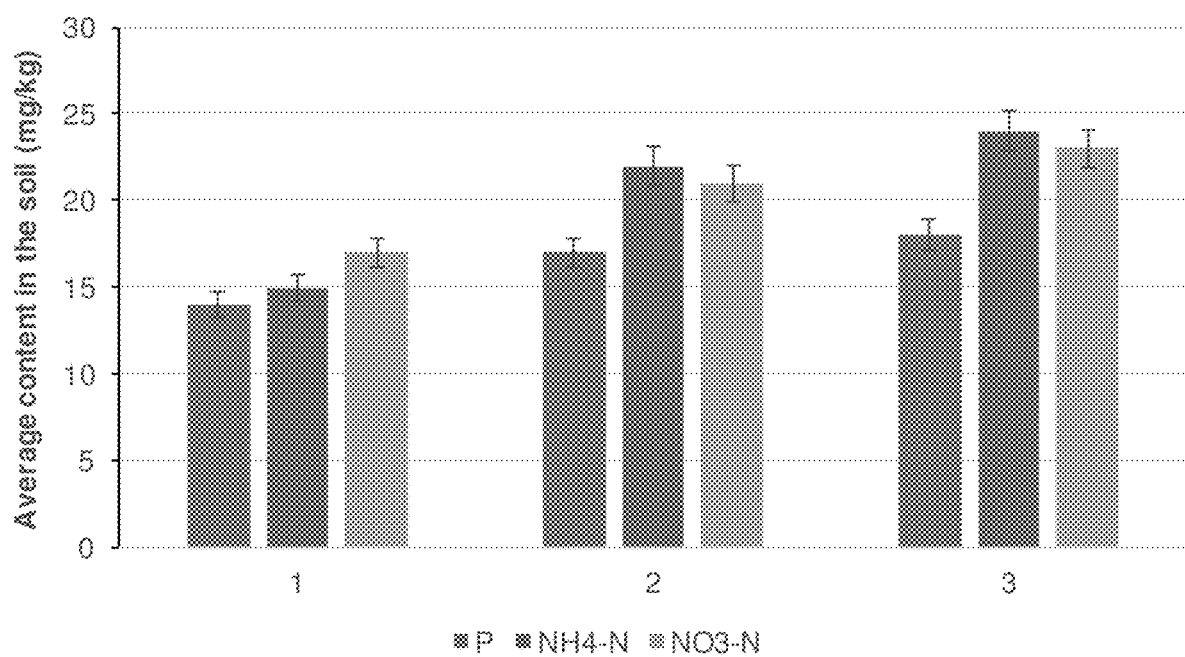
FIG. 11. Average content of phosphorus, ammonia nitrogen and nitrate nitrogen in the soil (mg/kg) inoculated with SAFE microbial mix with no nitrogen fertilization. Phosphorus (P) (first bar in each group), ammonia nitrogen (NH4-N) (second bar in each group) and nitrate nitrogen ($NO_3$—N) (third bar in each group) were measured 1: Before planting (June); 2: During the growing season (August); and 3: At harvest (September). The concentrations are measured in mg/kg.
Figure 13A:
FIG. 13A-13B. Photos of the corn experimental field deployment. A: Planting in June B: At harvest in September of the same year.
Figure 13B:
Figure 14A:
FIG. 14A-14I: Effect of *Pseudomonas fluorescens* GM41 on the growth of *Laccaria bicolor, Cenococcum* spp. PMI1 and *Hebeloma* spp. PMI1 in in vitro co-cultures. *P. fluorescens* GM41 co-culture has a positive effect on the growth of the three fungi included in the PMB microbial mixture.
Figure 14B:
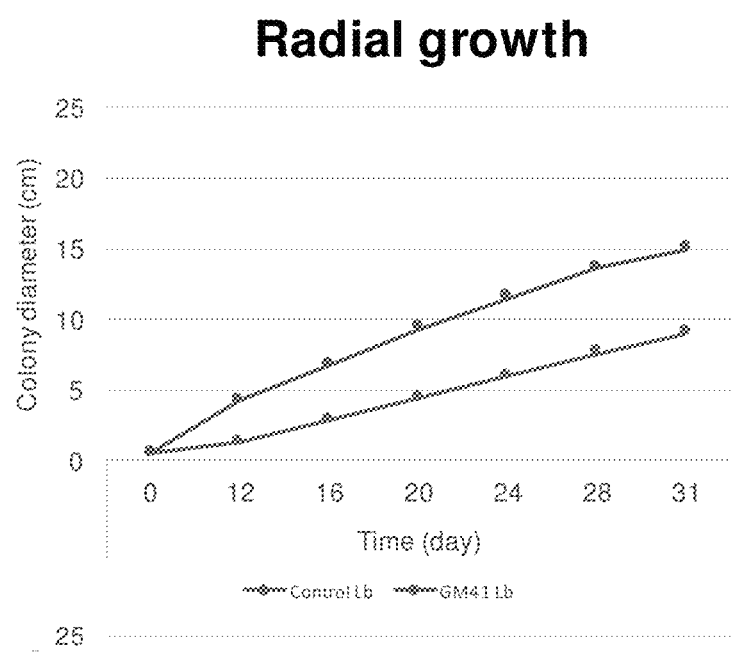
Figure 14C:
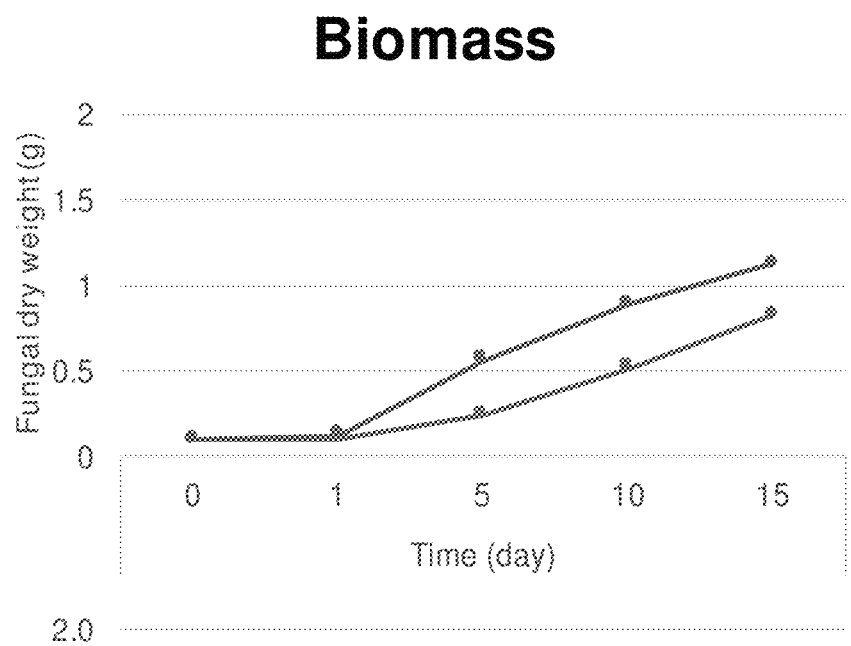
Figure 14D:
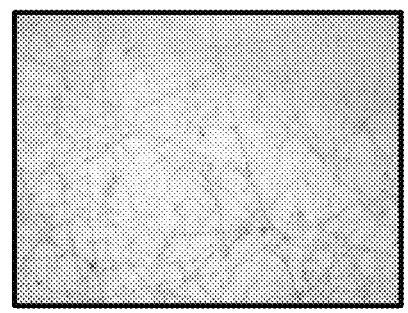
Figure 14E:
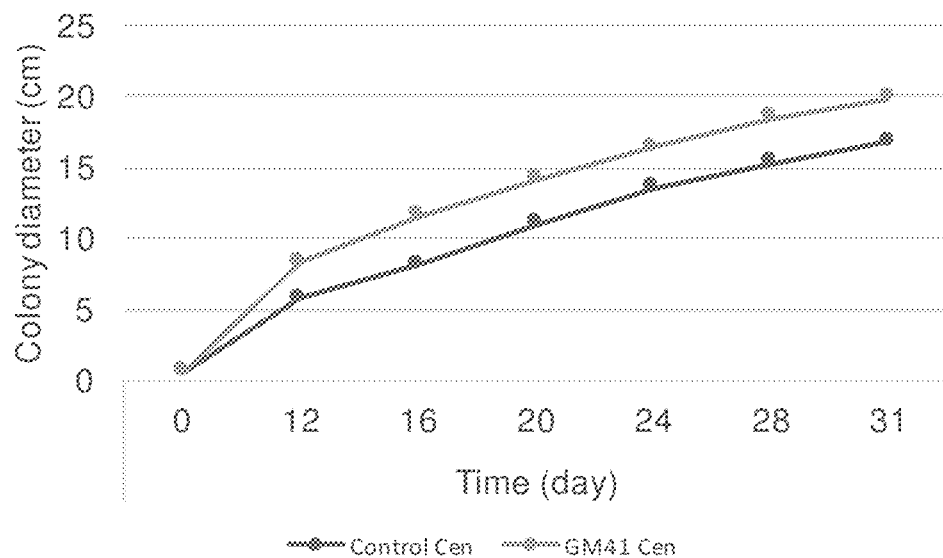
Figure 14F:
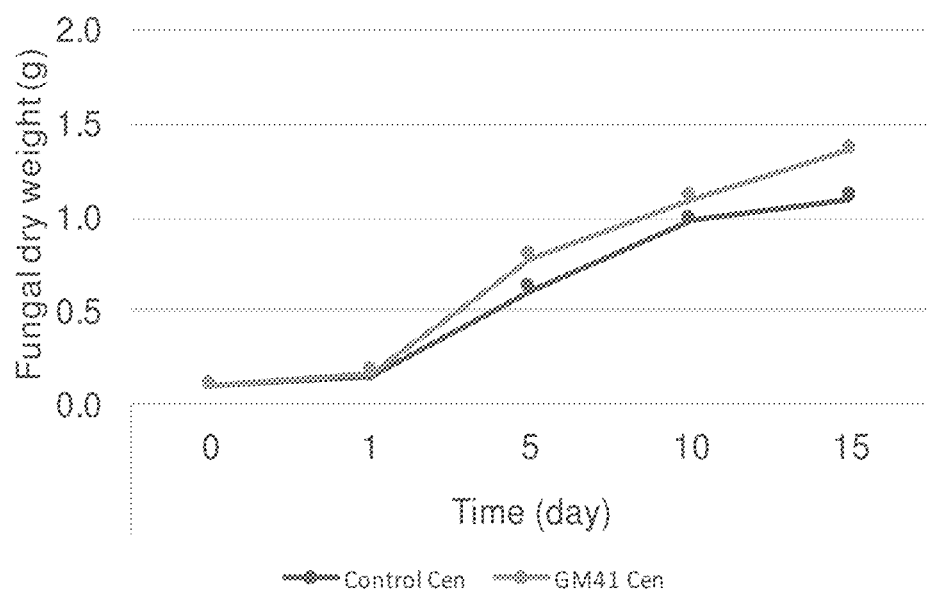
Figure 14G:
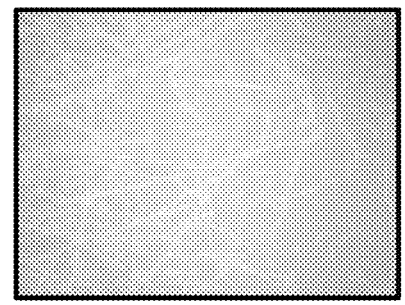
Figure 14H:
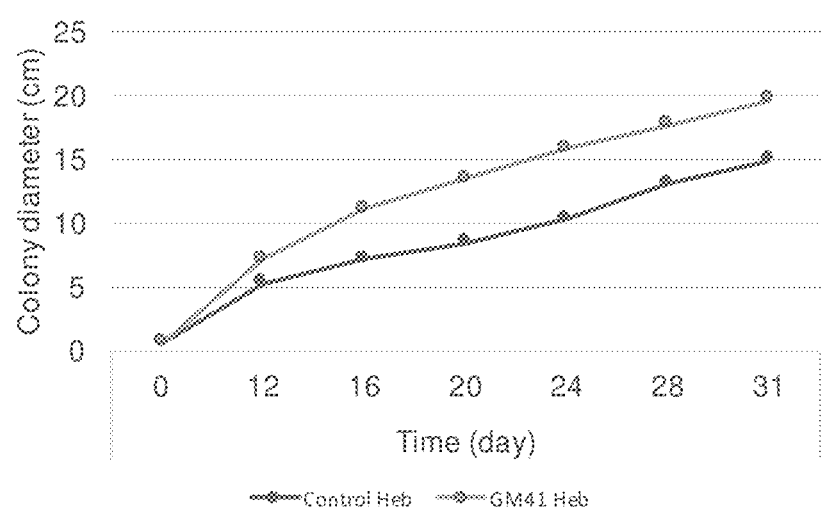
Figure 14I:
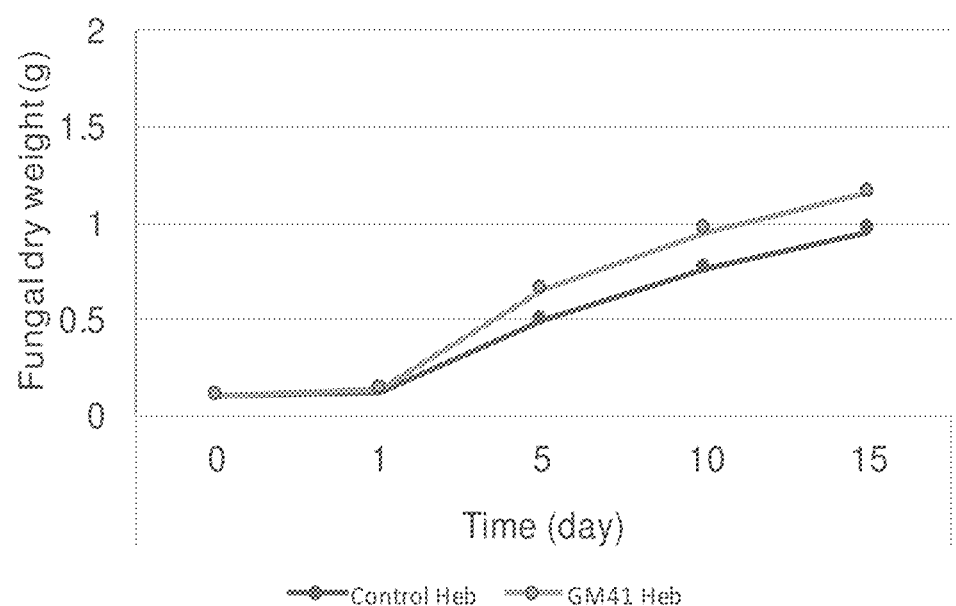

Results:

Application of *L. bicolor, P. indica* and *P. fluorescens* resulted in an increase in the nutritive qualities of a soil not fertilized with a nitrogen fertilizer as demonstrated by increasing phosphorus, ammonia nitrogen and nitrate nitrogen levels (FIG. 11) throughout the growing season (June through September) (FIG. 13).

Example 10: *Pseudomonas fluorescens* GM41 Enhances the Growth of *Laccaria bicolor, Cenococum* Spp. PMI1 and *Hebeloma* Spp. PMI1 in In Vitro Co-Cultures Materials and Methods:

Colony diameters (cm) and fungal dry weights (g) of the beneficial fungi *L. bicolor, Cenoccocum* spp. and *Hebeloma* spp. have been measured with or without co-culturing with *P. fluorescens* GM41 in vitro.

Results:

Co-culturing *P. fluorescens* GM41 with the beneficial fungi *L. bicolor, Cenoccocum* spp. and *Hebeloma* spp. positively affected the growth of the co-cultured fungi (FIG. 14).

Example 11: Positive Effects of Microbial Inoculants on *Populus tremula* X *P. alba* Growth Over 3 Months in Greenhouse Materials and Methods:

*Populus* plants (*Populus tremula* X *P. alba* species) were inoculated with mutualistic beneficial fungi such as *Laccaria bicolor*, the natural isolate *Hebeloma* spp. strain PMI1, the natural isolate of *Cenoccocum* spp. strain PMI, and *Pseudomonas fluorescens* strain GM41. The microbial mixture (PMB) used to treat *Populus* comprised 50 cells/ml of *Laccaria bicolor,* 50 cells/ml of *Hebeloma* spp. strain PMI1, 50 cells/ml of *Cenoccocum* spp. strain PMI1 and 1.4 million CFU/ml *Pseudomonas fluorescens* strain GM41. After 3 months of growth, aboveground fresh biomass, stem fresh biomass and leaf fresh biomass of the poplar were measured in plants treated with the microbial mixture and in non-treated control plants.

Figure 15:
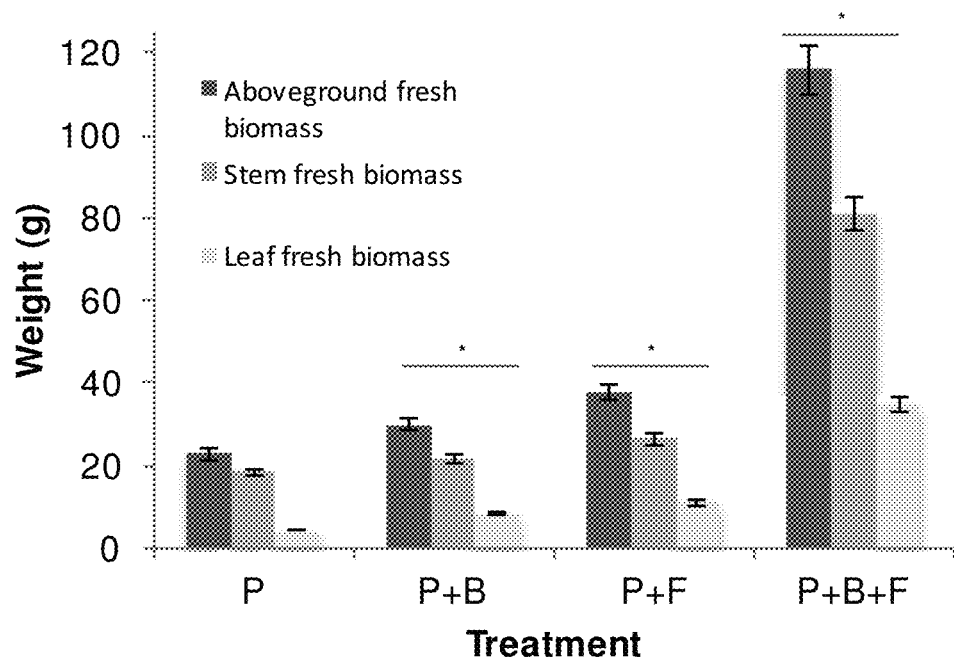
FIG. 15. Effects of microbial inoculants in *Populus tremula* X *P. alba* grown over 3 months in greenhouse. In each group of bars in the figure are, from left to right, aboveground fresh biomass, stem fresh biomass and leaf fresh biomass. P: *Populus* control plant; B: helper bacteria (*Pseudomonas fluorescens* GM41), F: fungal mixture of *Laccaria bicolor, Cenococcum* spp. PMI1 and *Hebeloma* spp. PMI1. Experiments were performed using 4 replicates of inoculated or non-inoculated *Populus* cuttings; * significantly different ANOVA p<0.05

Results:

Soil inoculation with PMB comprising *P. fluorescens* GM41 and/or with the fungal mixture of *Laccaria bicolor, Cenococcum* spp. PMI1 and *Hebeloma* spp. PMI1 stimulated the growth of total aboveground biomass (aboveground, stem and leaf biomass) of *Populus* as compared to the non-treated control *Populus* plants (FIG. 15).

Figure 16:
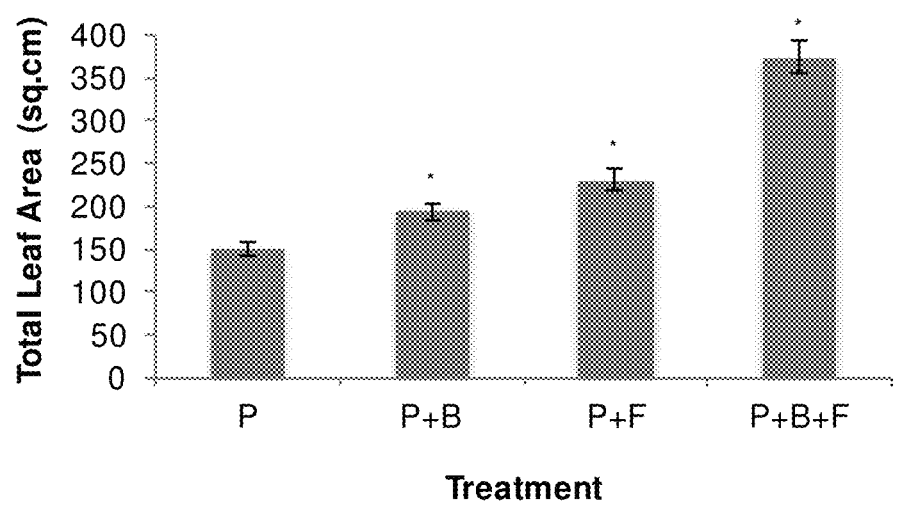
FIG. 16. Effects of microbial inoculants on the total leaf area in *Populus tremula* X *P. alba* grown over 3 months in greenhouse. P: *Populus* control plant; B: helper bacteria (*Pseudomonas fluorescens* GM41), F: fungal mixture of *Laccaria bicolor, Cenococcum* spp. PMI1 and *Hebeloma* spp. PMI1. Experiments were performed using 4 replicates of inoculated or non-inoculated *Populus* cuttings; * significantly different ANOVA p<0.05

The leaf area is a major determinant of photosynthesis assessing the growth potential of the plant. Therefore, the inventors wanted to measure the effect of PMB on total leaf area of *Populus* plants. Total surface area of all leaves per plant (*Populus tremula* X *P. alba*) were scanned and measured using WinRhizo/Winfolia scanner and software systems. The PMB microbial mixture (SAFE mixture) comprising *P. fluorescens* GM41 and/or with the fungal mixture of *Laccaria bicolor, Cenococcum* spp. PMI1 and *Hebeloma* spp. PMI1, was found to increase the total leaf surface area increasing then the potential capacity of the plant to produce more biomass as compared to their counterparts not treated with the PMB mixture (FIG. 16).

Example 12: PMB (SAFE) Inoculant Increases the Aboveground Biomass of P. trichocharpa and P. deltoides Under Well-Watered and Drought (−0.5 MPa to −1 MPa) Conditions Over 3 Months in Greenhouse Materials and Methods: Testing Drought Tolerance—
Experiments have been performed using 4 replicates of inoculated non-inoculated *Populus* cuttings. Initially, the well-watered *Populus* plants were stressed to −0.5 MPa, at which time they were re-watered to soil capacity. After the plants have been acclimated with three dry down cycles to −0.5 MPa, the plants were further dried down to a greater stress level of −1.0 MPa.

Figure 17:
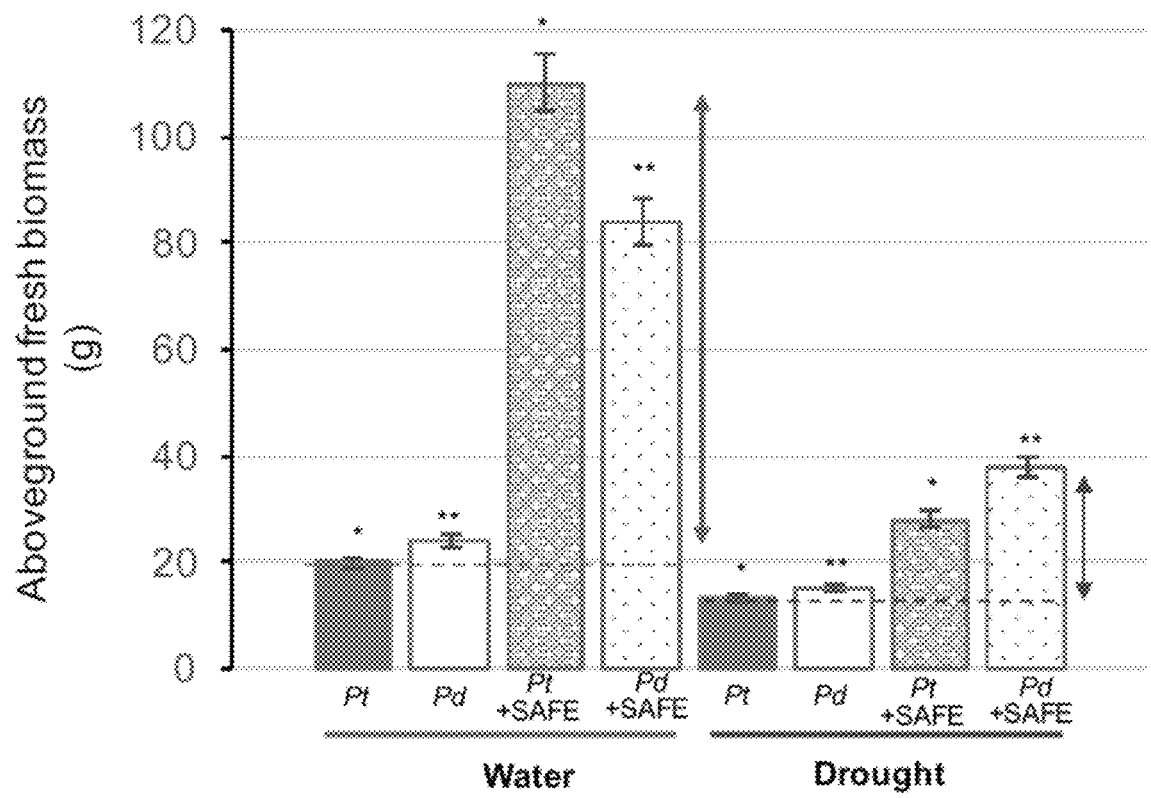
FIG. 17. Effects of SAFE inoculant on the aboveground biomass of *Populus trichocharpa* and *P. deltoides* under well-watered- and drought (−0.5 to −1 MPa) conditions over 3 months in greenhouse. In each group of bars, from left to right, are Pt: *P. trichocarpa*; Pd: *P. deltoides*; Pt+SAFE: mixture of *P. trichocarpa* and *Pseudomonas fluorescens* GM41, *Laccaria bicolor, Cenococcum* spp. PMI1 and *Hebeloma* spp. PMI1. Pd+SAFE: mixture of *P. deltoides* and *Pseudomonas fluorescens* GM41, *Laccaria bicolor, Cenococcum* spp. PMI1 and *Hebeloma* spp. PMI1. The group of bars on the left represent plants grown under well-watered conditions, and the group of bars on the right represent plants grown under drought conditions. Experiments were performed using 4 replicates of inoculated or non-inoculated *Populus* cuttings; *, ** significantly different ANOVA p<0.05.
Figure 18:
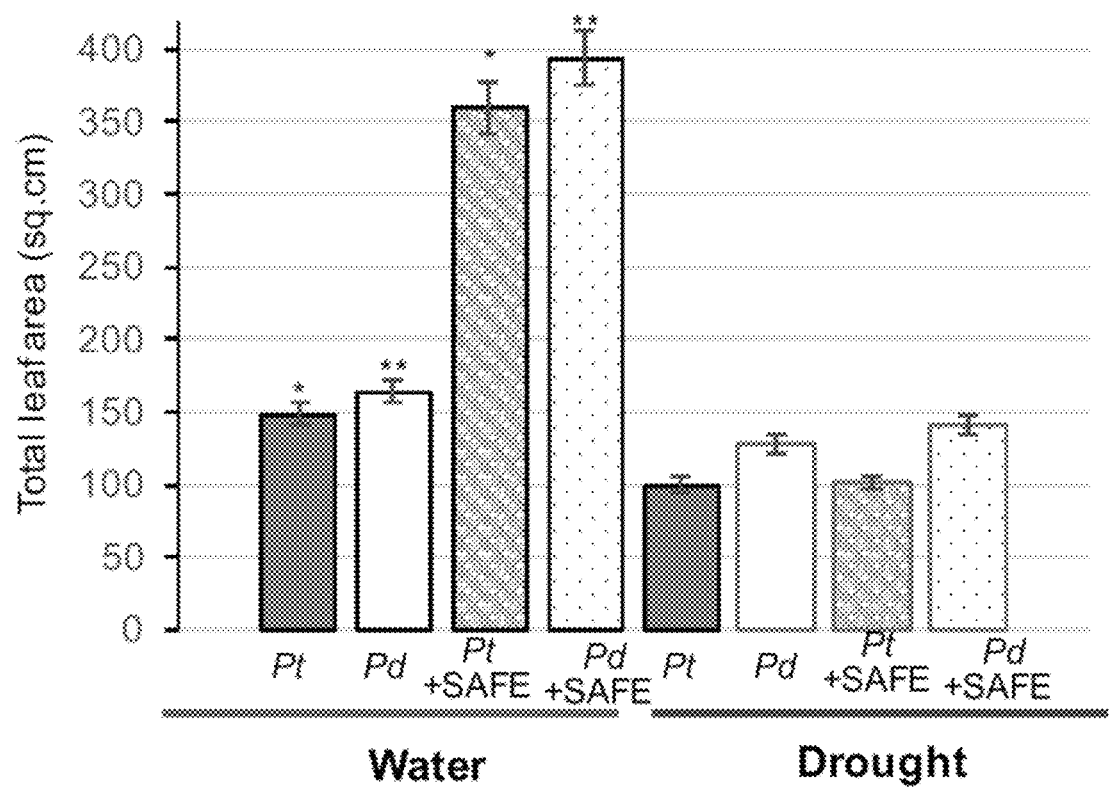
FIG. 18. Effects of SAFE inoculant on the total leaf area of *Populus trichocharpa* and *P. deltoides* under well-watered- and drought (−0.5 to −1 MPa) conditions over 3 months in greenhouse. In each group of bars are, from left to right, Pt: *P. trichocarpa*; Pd: *P. deltoides*; Pt+SAFE: mixture of *P. trichocarpa* and *Pseudomonas fluorescens* GM41, *Laccaria bicolor, Cenococcum* spp. PMI1 and *Hebeloma* spp. PMI1. Pd+SAFE: mixture of *P. deltoides*.

Results:
Inoculating different *Populus* strains with the PMB (aka. SAFE) mixture increased the aboveground biomass in well-watered condition as well as under drought stress in two different other *Populus* species (*P. trichocharpa* and *P. deltoides*) (FIG. 17). However, the PMB mixture (SAFE) did not increase the total leaf area in *Populus* plants under drought stress (FIG. 18, right bars), whereas it increased under normal (unrestricted) watering conditions (FIG. 18, left bars).

The inventors also investigated the fresh root biomass of *Populus* plants under well-watered and drought conditions. Inoculation with PMB increased the growth of fresh biomass in well-watered condition as well as under drought stress (FIG. 19). The PMB (SAFE) inoculant allowed the plant biomass increase observed in FIG. 16 by increasing root development and therefore allowing a better water supply under drought stress condition.

Using specific PCR primers, the inventors confirmed the presence, and therefore the persistence of each microbial strain of the PMB mixture (SAFE) in soil and on plant roots after three months.

Example 13: PMB (SAFE) Mixture Protects *Populus* Plants Against ROS Under Well-Watered and Drought Stress Consitions To measure possible effects of PMB on the stress caused by radical oxygen species (ROS), the inventors first measured the superoxide content of *P. trichocarpa* and *P. deltoides* leaves (FIG. 20A) and roots (FIG. 20B) under normal (well-watered) or stress (drought) conditions as described above. It was found that the superoxide radical content in *Populus* leaves were higher in drought conditions as well as well watered conditions in PMB (SAFE) mixture treated plants. On the other hand, the superoxide content in the roots were decreased under well-watered condition as well as under drought stress (FIG. 20A and FIG. 20B).

To minimize the damage from Radical Oxygen Species (ROS) plants utilize enzymatic antioxidants such as the Super Oxide Dismutase (SOD) and peroxidase (POD). It was found that both SOD (FIG. 21) and POD activity levels (FIG. 21) were increased in the leaves of *P. trichocharpa* and *P. deltoides* treated with the PMB mixture as compared to controls, under both well-watered and drought (−0.5 MPa to −1 MPa) conditions over 3 months in a greenhouse setting (FIG. 21 and FIG. 22).

Another plant defense mechanism against ROS damage is adjusting osmotic pressure by producing an osmoprotectant such as proline. The inventors measured proline levels in *Populus* leaves to see the effect of PMB in plant osmoprotection. As a result, it was found that inoculation the *Populus* plants with the PMB (SAFE) mixture in greenhouse increased the proline content in *Populus* leaves as compared to control plants, particularly under drought stress (FIG. 23).

Thus, the PMB (SAFE) inoculation facilitated protection against drought-induced stresses.

Example 14: PMB (SAFE) Positively Affects Plant Size and Survival in Field

*Populus* plants were planted in a field in Westport, Oreg. (FIG. 24), with or without PMB (SAFE) inoculation.

It was observed that plants treated with the microbial mixture grew more in size (FIG. 25A) and better survival percentage (FIG. 25B) than their non-treated counterparts after one month in the field.

After four months in the field, the PMB (SAFE) treated plants were taller (FIG. 26), and had a thicker stem (FIG. 27) as compared to their non-treated counterparts.

The current inventors have also shown in field that inoculation with the PMB (SAFE) mixture increased *Populus* root colonization by in situ beneficial microbes (FIG. 28). The presence and persistence of each strain of the SAFE microbes were assessed and confirmed on plant roots and surrounding soil by PCR amplification using specific designed PCR primers.

What is claimed is:
1. A composition comprising a *Laccaria bicolor* strain and a *Piriformospora indica* strain, wherein the *Laccaria bicolor* strain is present in the composition at about 85-115 cells per gram.
2. The composition of claim 1, wherein said composition includes about 100 fungal cells per gram of the composition.
3. The composition of claim 1, further comprising a *Pseudomonas fluorescens* strain.
4. The composition of claim 3, wherein said *Pseudomonas fluorescens* strain is the strain designated as GM41 (ATCC PTA-122788).
5. The composition of claim 3, wherein said *Pseudomonas fluorescens* strain is present in the composition at a concentration between $1 \times 10^2$ CFU/mL and $1.6 \times 10^6$ CFU/mL.
6. The composition of claim 5, wherein said composition is a liquid-formulation and further comprises components suitable for plant growth.
7. The composition of claim 1, further comprising a binding agent selected from the group consisting of pullulan, paraffin, pitch and calcium nitrate.
8. The composition of claim 1, wherein the *Piriformospora indica* strain is present in the composition at about 50 cells per gram.
9. A method comprising treating plants with the composition according to claim 1.

* * * * *